(12) United States Patent
Zu et al.

(10) Patent No.: US 8,858,813 B2
(45) Date of Patent: Oct. 14, 2014

(54) PATTERNING PROCESS

(75) Inventors: Lijun Zu, Woodbury, MN (US);
Matthew H. Frey, Cottage Grove, MN (US); Suresh S. Iyer, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 428 days.

(21) Appl. No.: 13/130,320

(22) PCT Filed: Dec. 2, 2009

(86) PCT No.: PCT/US2009/066358
§ 371 (c)(1),
(2), (4) Date: May 20, 2011

(87) PCT Pub. No.: WO2010/068535
PCT Pub. Date: Jun. 17, 2010

(65) Prior Publication Data
US 2011/0226733 A1    Sep. 22, 2011

Related U.S. Application Data

(60) Provisional application No. 61/121,598, filed on Dec. 11, 2008, provisional application No. 61/121,605, filed on Dec. 11, 2008.

(51) Int. Cl.
| | |
|---|---|
| *C03C 15/00* | (2006.01) |
| *C07C 323/60* | (2006.01) |
| *B05D 1/18* | (2006.01) |
| *B82Y 30/00* | (2011.01) |
| *B82Y 40/00* | (2011.01) |
| *C07C 323/41* | (2006.01) |
| *C07C 323/52* | (2006.01) |
| *C08G 65/00* | (2006.01) |
| *C08G 65/334* | (2006.01) |
| *C09D 171/02* | (2006.01) |
| *G03F 7/00* | (2006.01) |

(52) U.S. Cl.
CPC ............. *C07C 323/60* (2013.01); *B05D 1/185* (2013.01); *B82Y 30/00* (2013.01); *B82Y 40/00* (2013.01); *C07C 323/41* (2013.01); *C07C 323/52* (2013.01); *C08G 65/007* (2013.01); *C08G 65/334* (2013.01); *C09D 171/02* (2013.01); *G03F 7/0002* (2013.01)
USPC ............................................. 216/37; 216/96

(58) Field of Classification Search
None
See application file for complete search history.

(56) References Cited

U.S. PATENT DOCUMENTS

| 3,250,807 A | 5/1966 | Fritz et al. |
| 3,250,808 A | 5/1966 | Moore et al. |

(Continued)

FOREIGN PATENT DOCUMENTS

| JP | 10-124844 | 5/1998 |
| WO | WO 02/50583 A2 | 6/2002 |

(Continued)

OTHER PUBLICATIONS

Michel, Printing Meets Lithography, 2002, American Institute of Physics, Aug./Sep. issue, p. 16-19.*

(Continued)

*Primary Examiner* — Binh X Tran
*Assistant Examiner* — David Cathey, Jr.
(74) *Attorney, Agent, or Firm* — Lucy C. Weiss

(57) ABSTRACT

A patterning process comprises (a) providing at least one substrate having at least one major surface; (b) providing at least one patterning composition comprising at least one functionalizing molecule that is a perfluoropolyether organosulfur compound; (c) applying the patterning composition to the major surface of the substrate in a manner so as to form at least one functionalized region and at least one unfunctionalized region of the major surface; and (d) etching at least a portion of the unfunctionalized region.

18 Claims, 4 Drawing Sheets

40μm

(56) References Cited

U.S. PATENT DOCUMENTS

| | | | |
|---|---|---|---|
| 3,810,874 | A | 5/1974 | Mitsch et al. |
| 4,022,928 | A | 5/1977 | Piwcyzk |
| 4,204,064 | A | 5/1980 | Kalopissis |
| 4,845,268 | A | 7/1989 | Ohsaka et al. |
| 4,882,216 | A * | 11/1989 | Takimoto et al. ............. 428/209 |
| 4,904,417 | A | 2/1990 | Ohsaka et al. |
| 5,182,342 | A | 1/1993 | Feiring et al. |
| 5,354,922 | A | 10/1994 | Marchionni et al. |
| 5,446,182 | A | 8/1995 | Bruening et al. |
| 5,512,131 | A | 4/1996 | Kumar et al. |
| 6,395,867 | B1 | 5/2002 | Maignan |
| 6,399,729 | B1 | 6/2002 | Farnham et al. |
| 6,518,168 | B1 | 2/2003 | Clem et al. |
| 6,923,921 | B2 | 8/2005 | Flynn et al. |
| 6,991,826 | B2 | 1/2006 | Pellerite et al. |
| 7,041,232 | B2 | 5/2006 | Bietsch et al. |
| 7,148,360 | B2 | 12/2006 | Flynn et al. |
| 7,160,583 | B2 | 1/2007 | Frey et al. |
| 7,335,786 | B1 | 2/2008 | Iyer et al. |
| 7,678,426 | B2 | 3/2010 | Flynn et al. |
| 7,745,653 | B2 | 6/2010 | Iyer et al. |
| 7,825,272 | B2 | 11/2010 | Iyer et al. |
| 7,968,804 | B2 | 6/2011 | Frey et al. |
| 2003/0013923 | A1 | 1/2003 | Marchionni et al. |
| 2003/0194873 | A1* | 10/2003 | Imada et al. ................. 438/700 |
| 2003/0207215 | A1* | 11/2003 | Xu et al. ........................ 430/321 |
| 2004/0241396 | A1 | 12/2004 | Jing et al. |
| 2005/0098433 | A1* | 5/2005 | Gundel .................... 204/403.02 |
| 2005/0194588 | A1* | 9/2005 | Sasaki et al. .................... 257/40 |
| 2005/0221271 | A1* | 10/2005 | Murphy et al. ................... 435/4 |
| 2005/0250921 | A1 | 11/2005 | Qiu et al. |
| 2006/0035129 | A1* | 2/2006 | Nomura et al. ................. 429/33 |
| 2007/0292679 | A1 | 12/2007 | Pellerite et al. |
| 2008/0095985 | A1 | 4/2008 | Frey et al. |
| 2008/0315459 | A1 | 12/2008 | Zhang et al. |
| 2009/0025727 | A1 | 1/2009 | Klun et al. |
| 2009/0028910 | A1 | 1/2009 | DeSimone et al. |
| 2009/0061152 | A1 | 3/2009 | DeSimone et al. |
| 2009/0069193 | A1* | 3/2009 | Flemming et al. ................ 506/9 |
| 2009/0218310 | A1 | 9/2009 | Zu et al. |
| 2010/0219367 | A1 | 9/2010 | Dams et al. |
| 2010/0221967 | A1 | 9/2010 | Iyer et al. |
| 2010/0258968 | A1 | 10/2010 | Zu et al. |

FOREIGN PATENT DOCUMENTS

| | | |
|---|---|---|
| WO | WO 02/92660 | 11/2002 |
| WO | WO 2005/101466 | 10/2005 |
| WO | WO 2005/113642 | 12/2005 |
| WO | WO 2007/146855 | 12/2007 |
| WO | WO 2008/024207 A1 | 2/2008 |
| WO | WO 2010/068531 | 6/2010 |

OTHER PUBLICATIONS

Transene, Etchants,Feb. 5, 2014, Transene, p. 1-4.*
Alamarguy et al., Corrosion Behavior of Gold Surfaces Protected With Bonded Perfluoro Polyethers, Surf. Interface Anal. 36, 780 (2004).
Alamarguy et al., Surface Investigations of Bonded Perfluoro Polyether Monolayers on Gold Surfaces, Surf. Interface Anal. 36, 1210 (2004).
Blixt et al., Solid-Phase Enzymatic Synthesis of a Sialyl Lewis X Tetrasaccharide on a Sepharose Matrix, J. Org. Chem. 63, 2705 (1998).
Burdinski et al., Thiosulfate—and Thiosulfonate-Based Etchants for the Patterning of Gold Using Microcontact Printing, Chemistry of Materials 19, 3933 (2007).
Clegg et al., Control of Monolayer Assembly Structure by Hydrogen Bonding Rather Than by Adsorbate-Substrate Templating, Journal of the American Chemical Society 121, 5319 (1999).
Clegg et al., Self-Assembled Monolayers Stabilized by Three-Dimensional Networks of Hydrogen Bonds, J. Am. Chem. Soc. 120, 2486 (1998).
Clegg et al., The Interplay of Lateral and Tiered Interactions in Stratified Self-Organized Molecular Assemblies, Langmuir 15, 8876 (1999).
Colorado et al., Wettabilities of Self-Assembled Monolayers on Gold Generated From Progressively Fluorinated Alkanethiols, Langmuir 19, 3288 (2003).
Eidelloth et al, Wet Etching of Gold Films Compatible With High TC Superconducting Thin Films, Applied Physics Letters 59(13), 1632 (1991).
Evans et al., XPS Imaging of Patterned Self-Assembled Monolayers Containing Perfluorinated Alkyl Chains, Surf. Interface Anal. 24, 187 (1996).
Geissler et al., Fabrication of Metal Nanowires Using Microcontact Printing, Langmuir 19, p. 6301 (2003).
Graupe et al., Oriented Surface Dipoles Strongly Influence Interfacial Wettabilities, J. Am. Chem. Soc. 121, 3222 (1999).
J. P. Rolland et al., High-Resolution Soft Lithography: Enabling Materials for Nanotechnologies, Angewandte Chemie 43, 5796 (2004).
Kopf et al., Chemical Imaging of Microstructured Self-Assembled Monolayers With Nanometer Resolution, J. Phys. Chem. C 111, p. 8166 (2007).
Kumar et al., Features of Gold Having Micrometer to Centimeter Dimensions Can Be Formed Through a Combination of Stamping With an Elastomeric Stamp and an Alkanethiol "Ink" Followed by Chemical Etching, Appl. Phys. Lett. 63(14), p. 2002 (1993).
Laibinis et al., Comparison of the Structures and Wetting Properties of Self-Assembled Monolayers on N-Alkanethiols on the Coinage Metal Surfaces, Cu, Ag, Au, J. Am. Chem. Soc. 113(19), p. 7152 (1991).
Latham et al., Versatile Routes Toward Functional, Water-Soluble Nanoparticles Via Trifluoroethylester-Peg-Thiol Ligands, Langmuir 22, 4319 (2006).
Lee et al., Solvent Compatibility of Poly(Dimethylsiloxane)-Based Microfluidic Devices, Analytical Chemistry vol. 75, pp. 6544-6554 (2003).
Lenk et al., Structural Investigation of Molecular Organization in Self-Assembled Monolayers of a Semifluorinated Amidethiol, Langmuir 10, 4610 (1994).
Libioulle et al., Contact-Inking Stamps for Microcontact Printing of Alkanethiols on Gold, Langmuir vol. 15, pp. 300-304 (1999).
Love et al., Self-Assembled Monolayers of Thiolates on Metals As a Form of Nanotechnology, Chemical Reviews vol. 105, pp. 1103-1169 (2005).
Luscombe et al., Synthesis of Supercritical Carbon Dioxide Soluble Perfluorinated Dendrons for Surface Modification, J. Org. Chem. (2007).
Masuda et al., Visualization of DNA Hybridization on Gold Thin Film by Utilizing the Resistance Effect of DNA Monolayer, Sensors and Actuators B 105, 556 (2005).
Michel et al., Printing Meets Lithography: Soft Approaches to High-Resolution Patterning, IBM J. Res. & Dev. 45(5), p. 697 (2001).
Naud et al., Critical Influence of the Fluorinated Chain Length in the Self-Assembly of Terminally Perfluorinated Alkanethiol Monolayers on Gold Surfaces. An Electrochemical Study, Langmuir 17, 4851 (2001).
Paulini et al., Effects of Branched Ligands on the Structure and Stability of Monolayers on Gold Nanoparticles, Langmuir 18, 2368 (2002).
Ramette et al., Thermodynamics of Iodine Solubility and Triiodide Ion Formation in Water and in Deuterium Oxide, Journal of the American Chemical Society 87(22), 5001 (1965).
Rogers et al., Paper-Like Electronic Displays: Large-Area Rubber-Stamped Plastic Sheets of Electronics and Microencapsulated Electrophoretic Inks, PNAS 98(9), p. 4835 (2001).
Saunders et al., Solvent Density-Dependent Steric Stabilization of Perfluoropolyether-Coated Nanocrystals in Supercritical Carbon Dioxide, J. Phys. Chem., B 2004, 108(41), pp. 15969-15975.
Smith et al., Phase Separation Within a Binary Self-Assembled Monolayer on Au{111} Driven by an Amide-Containing Alkanethiol, J. Phys. Chem. 105, 1119 (2001).

(56) References Cited

OTHER PUBLICATIONS

Solvents and Solvent Effects in Organic Chemistry, Second Edition, C. Reichardt, VCH Verlagsgesellschaft mbH, Germany (1988).

Srinivas et al., Bioanalytical Considerations for Compounds Containing Free Sulfhydryl Groups, Biomedical Chromotography vol. 17, pp. 285-291 (2003).

Svedhem et al., Synthesis of a Series of Oligo(Ethylene Glycol)-Terminated Alkanethiol Amides Designed to Address Structure and Stability of Biosensing Interfaces, J. Org. Chem. 66, 4494 (2001).

Takwa et al., One-Pot Difunctionalization of Poly(Omega-Pentadecalactone) With Thiol-Thiol or Thiol-Acrylate Groups, Catalyzed by Candida Antarctica Lipase B, Macromol. Rapid Commun. 27, 1932 (2006).

Williams et al., Etch Rates for Micromachining Processing—Part II, J. Microelectromechanical Systems 12(6), p. 761 (2003).

Xia et al., A Selective Etching Solution for Use With Patterned Self-Assembled Monolayers of Alkanethiolates on Gold, Chem. Mater. 7, 2332 (1995).

Yazdi et al., Design of Highly CO2-Soluble Chelating Agents for Carbon Dioxide Extraction of Heavy Metals, J. Mater. Res., 1995, 10(3), pp. 530-537.

Research Disclosures, No. 40576, p. 81 (Jan. 1998).

International Search Report for PCT Application No. PCT/US2009/066358, mailed Mar. 5, 2010.

Supplementary European Search Report for EP 09832396.7 (PCT/US2009/066358), mailed on Apr. 10, 2013, 2 pages.

Ghosh, Moniraj et al., "Multifunctional Surfaces with Discrete Functionalized Regions for Biological Applications," Langmuir, 2008, vol. 24, No. 15, pp. 8134-8142.

Zhou, Xiaozhu et al, "Chemically Functionalized Surface Patterning," Small, 2011, vol. 7, No. 16, pp. 2273-2289.

\* cited by examiner

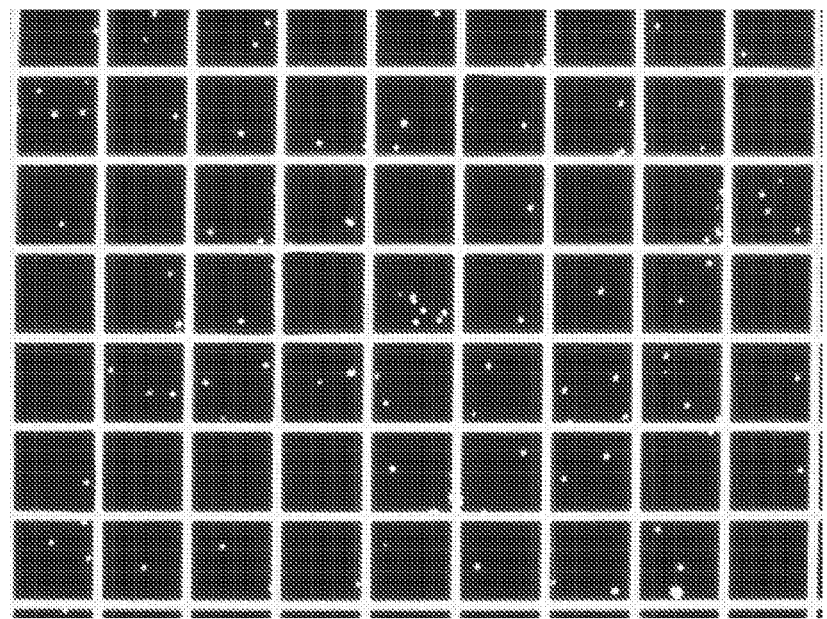
*Fig. 1*  80μm
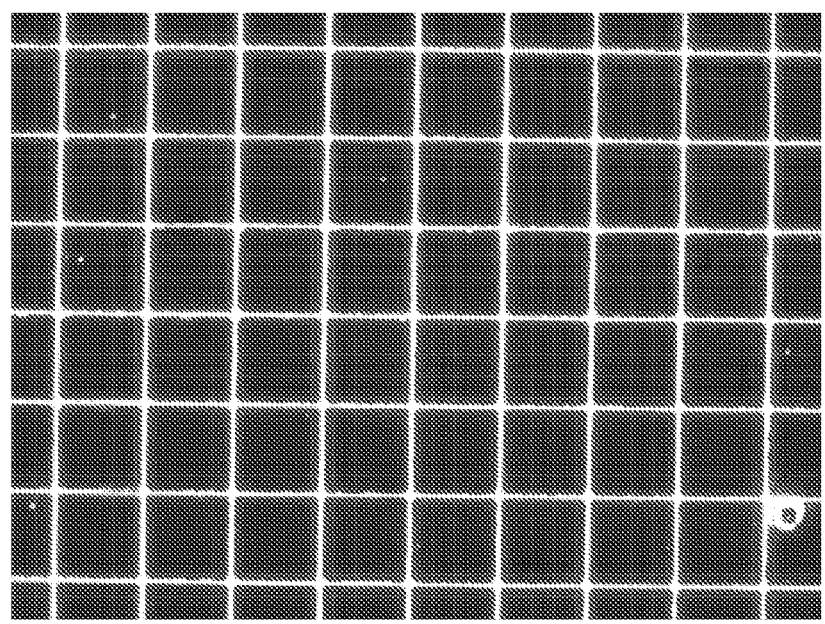
*Fig. 2*  80μm

80μm

80μm

PATTERNING PROCESS

STATEMENT OF PRIORITY

This application claims the priorities of U.S. Provisional Applications Nos. 61/121,605 and 61/121,598, both filed Dec. 11, 2008, the contents of which are hereby incorporated by reference.

FIELD

This invention relates to processes for patterning functionalizing molecules on substrates.

BACKGROUND

Self-assembled monolayers (SAMs) can form by the spontaneous adsorption of functionalizing molecules from a solution or a gas onto a substrate (for example, a metal or a metal oxide) in a single layer. SAM-forming molecules generally comprise a headgroup, which can interact with the substrate, while the remaining portion of the molecule can acquire some order from its interaction with neighboring molecules in the monolayer. For example, the molecules can be attached by a chemical bond to the substrate surface and can adopt a preferred orientation with respect to that surface and even with respect to each other.

SAMs can form on a variety of types of substrates (including those comprising a coating on a physical support) depending upon the specific chemical and/or physical nature of the headgroup. For example, alkylthiols and disulfides can form SAMs on gold, silver, palladium, and copper, and silanes can form SAMs on silicon oxide. The preparation, characterization, and utilization of SAMs has been an important field of research because of the ability of SAMs to change and control the properties (for example, the wetting, lubrication, and/or corrosion properties) of substrate surfaces.

Various techniques have been used for patterning self-assembled monolayers on substrate surfaces. Many of these techniques have involved first covering the substrate entirely with a SAM and then removing the SAM in some areas by using, for example, ultraviolet light, an electron beam, bombarded atoms, or the probe of a scanning probe microscope (scanning tunneling microscope or atomic force microscope). Another patterning technique called microcontact printing (µCP) has been used to form a SAM on desired areas of a substrate surface during a printing step (for example, with printed feature sizes of less than one micrometer being achievable). The patterned SAMs resulting from such patterning techniques have then served as resists for selectively etching the substrates.

Microcontact printing SAMs generally involves applying an ink composition comprising functionalizing molecules to a relief-patterned elastomeric stamp (for example, a poly (dimethylsiloxane) (PDMS) stamp) and then contacting the inked stamp to a substrate surface, usually a metal (for example, gold, silver, palladium, or copper) or metal oxide (for example, indium-tin oxide) surface, so that SAMs form in the regions of contact between the stamp and the substrate. It has been relatively simple to use microcontact printing to change the surface properties (for example, the wetting characteristics) of a substrate, and, although it has been possible to employ microcontact printing for the chemical etch-patterning of substrates (for example, relatively thin gold films) with high contrast and resolution, such methods have generally required the use of chemical etchants with certain undesirable characteristics that have limited commercial implementation. Specifically, heretofore it has not been possible to etch pattern metal substrates (including metal-coated physical supports) using microcontact printed SAM mask patterns in combination with chemical etchants having desirably long lifetimes and desirably high etch rates and etch capacities.

Even high quality SAMs having relatively few defects can be ineffective in providing etch protection, if the molecules forming the SAMs lack resistance to the chemical etchants that are utilized. Potassium iodide/iodine-based etchants (KI/$I_2$; a "tri-iodide" etchant) are commercially available and offer a compelling combination of stability (for example, for periods of weeks), speed (for example, etch rates of about 25-660 nanometers per minute), capacity (for example, greater than about 20 grams of metal dissolved per liter of etchant solution), and safety. The SAM-forming molecules typically used in etch-patterning, however, generally do not exhibit sufficient resistance to tri-iodide etchants to enable effective patterning. Specifically, for the SAM-forming molecules used with such etchants to date, metal underlying a patterned SAM generally has been etched essentially as rapidly as metal not covered by the SAM.

Conventional SAMs have shown resistance to a variety of other chemical etchants that have been used for etching gold (including cyanide/oxygen-, ferrocyanide/ferricyanide-, and thiourea-based etchant systems), but these etchants have their own deficiencies. Cyanide/oxygen-based systems are generally relatively slow (for example, etch rates of about 2-3 nanometers per minute) and can present toxicity issues. Ferrocyanide/ferricyanide mixtures can be less toxic than etchants based upon free cyanide but also are relatively slow (for example, etch rates of about 2-4 nanometers per minute) and of relatively low capacity. Thiourea-based etchants with ferric ions as oxidizing species are relatively stable (for example, several hours of stable activity) but relatively slow (for example, etch rates of about 10 nanometers per minute for gold). Thiourea-based etchants with hydrogen peroxide as oxidizing species are relatively faster (for example, etch rates of about 100 nanometers per minute for gold) but are relatively unstable (for example, stable for periods of only minutes to hours).

SUMMARY

In view of the foregoing, we recognize that there is a need for patterning processes (and compositions for use therein) that can be used effectively for the etch-patterning of substrates (for example, the chemical etch-patterning of metals and metal oxides) with relatively high contrast and resolution and, preferably, with sufficient speed so as to be relatively commercially viable.

Briefly, in one aspect, this invention provides a patterning process. The process comprises (a) providing at least one substrate (preferably, a substrate comprising at least one elemental metal, at least one metal alloy, at least one metal-containing compound, or a combination thereof) having at least one major surface; (b) providing at least one patterning composition comprising at least one functionalizing molecule that is a perfluoropolyether organosulfur compound (for example, a perfluoropolyether thiol compound); (c) applying the patterning composition to the major surface of the substrate in a manner so as to form at least one functionalized region (preferably, comprising a self-assembled monolayer (SAM) of the functionalizing molecule) and at least one unfunctionalized region of the major surface; and (d) etching (preferably, by chemical etching) at least a portion of the unfunctionalized region (preferably, selectively). Preferably, the patterning composition is applied by printing (more preferably, by microcontact printing). The functionalizing molecule is preferably an amide-linked perfluoropolyether organosulfur compound (more preferably, an amide-linked perfluoropolyether thiol compound).

It has been discovered that perfluoropolyether organosulfur compounds can be applied in a pattern onto (to thereby functionalize or modify the properties of) various substrates including, for example, metals. The resulting patterns can then be used as resists for etch-patterning the substrates.

Surprisingly, the perfluoropolyether organosulfur compounds can form functionalized regions (preferably, comprising a self-assembled monolayer (SAM) of the functionalizing molecules) that can exhibit relatively greater resistance to tri-iodide etchants for gold (and thereby relatively greater etching selectivity) than the resistance exhibited by conventional SAMs (for example, SAMs formed from alkylthiols). The perfluoropolyether organosulfur compounds (especially those that are amide-linked) can be used to form patterning compositions that can be microcontact printed with relatively high fidelity on gold surfaces to yield patterned masks that are "tri-iodide etchant compatible." Such compatibility with tri-iodide etchants can enable chemical etching of the patterned substrates to be carried out with enhanced process speed and therefore enhanced industrial utility, relative to processes using conventional SAMs and/or conventional chemical etchants (for example, cyanide/oxygen-, ferrocyanide/ferricyanide-, and thiourea-based etchant systems).

Thus, in at least preferred embodiments, the process of the invention can meet the above-referenced need for patterning processes that can be used effectively for the etch-patterning of substrates (for example, the chemical etch-patterning of metal coatings on insulating supports) with relatively high contrast and resolution and, preferably, with sufficient speed so as to be relatively commercially viable. The process can be used to micropattern conductor coatings (for example, gold, silver, or palladium thin film) on insulating or semiconducting physical supports (for example, glass, plastic, or silicon supports) for use in making displays and display components, flexible electronics, sensors, and electronic devices for use in computing, communications, personal safety, medical diagnostics, and anti-counterfeiting applications.

BRIEF DESCRIPTION OF DRAWING

These and other features, aspects, and advantages of the present invention will become better understood with regard to the following description, appended claims, and accompanying drawing, wherein:

FIG. 1 is an optical photomicrograph (transmission mode) of the resulting gold-micropatterned substrate of Example 7 (dark region is gold).

FIG. 2 is an optical photomicrograph (transmission mode) of the resulting gold-micropatterned substrate of Example 8 (dark region is gold).

DETAILED DESCRIPTION

Figure 3:
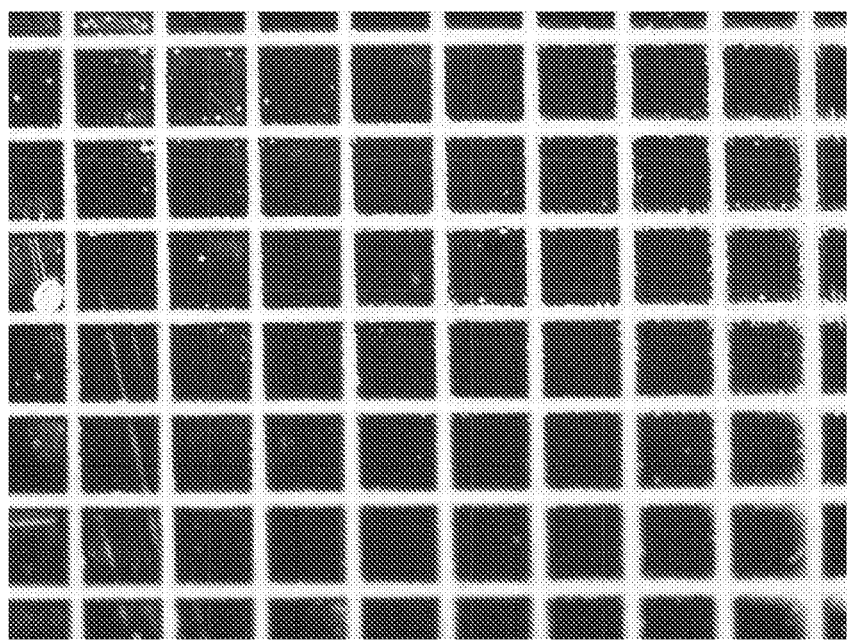
FIG. 3 is an optical photomicrograph (transmission mode) of the resulting gold-micropatterned substrate of Example 9 (dark region is gold).

In the following detailed description, various sets of numerical ranges (for example, of the number of carbon atoms in a particular moiety, of the amount of a particular component, or the like) are described, and, within each set, any lower limit of a range can be paired with any upper limit of a range.

Definitions

As used in this patent application:

"amide-linked" means comprising at least one carbonylimino moiety (as defined below);

"catenated heteroatom" means an atom other than carbon (for example, oxygen, nitrogen, or sulfur) that is bonded to carbon atoms in a carbon chain so as to form a carbon-heteroatom-carbon chain;

"carbonylimino" means a divalent group or moiety of formula —C(=O)—N(R)—, wherein R is hydrogen or alkyl (for example, selected from alkyl groups having from one to about four carbon atoms);

"carbonyloxy" means a divalent group or moiety of formula —C(=O)O—;

"carbonylthio" means a divalent group or moiety of formula —C(=O)S—;

"dithio" means a divalent group or moiety of formula —S—S—;

"etch" means to remove material from a substrate by chemical reaction, dissolution, or a combination thereof (for example, by contacting the material with a wet chemical solution that dissolves the material or reacts with the material to yield soluble products);

"fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom;

"fluorochemical" means fluorinated or perfluorinated;

"heteroalkylene" means an alkylene group or moiety containing at least one catenated heteroatom;

"mercapto" means a monovalent group or moiety of formula —SH;

"oxythiocarbonylthio" means a divalent group or moiety of formula —O—C(=S)S—;

"perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine;

"perfluoroether" means a group or moiety having two saturated or unsaturated perfluorocarbon groups (linear, branched, cyclic (preferably, alicyclic), or a combination thereof) linked with an oxygen atom (that is, there is one catenated oxygen atom);

"perfluoropolyether segment" means a group or moiety having three or more saturated or unsaturated perfluorocarbon groups (linear, branched, cyclic (preferably, alicyclic), or a combination thereof) linked with oxygen atoms (that is, there are at least two catenated oxygen atoms);

"sulfonamido" means a divalent group or moiety of formula —SO$_2$N(R')—, wherein R' is hydrogen or alkyl (for example, selected from alkyl groups having from one to about four carbon atoms); and "thio" means a divalent group or moiety of formula —S—.

Substrate

Substrates suitable for use in the process of the invention include those having at least one surface comprising a material that is capable of supporting a pattern of perfluoropolyether organosulfur compounds as functionalizing molecules. Preferably, the perfluoropolyether organosulfur compounds are supported on the material through a chemical interaction. Suitable substrates can comprise a single material or a combination of different materials and can be homogeneous or heterogeneous in nature. Useful heterogeneous substrates include coated substrates comprising a coating of a material (for example, a metal) borne on a physical support (for example, a polymer film). In some embodiments, the substrate is substantially smooth (preferably, with average roughness (Ra) less than about 5 nanometers (nm)).

In some embodiments, the substrate comprises at least one substantially planar surface. Substantially planar surfaces include surfaces with relatively low curvature (for example, less than about 0.03 cm$^{-1}$). Substantially planar surfaces also include a major surface of a flexible film or sheet substrate, as well as the exposed surface of a coating applied to a physical support in the form of a rigid article with a surface having relatively low curvature or a physical support in the form of a flexible film or sheet.

Useful substrates include those that comprise at least one inorganic material (for example, a metallic or metal-containing compound material, including polycrystalline materials) alone or as a coating on a physical support such as, for example, a polymer film or a glass or silicon wafer. The inorganic material can include, for example, elemental metal, metal alloys, metal-containing compounds (for example, intermetallic compounds, metal oxides, metal sulfides, metal carbides, and metal nitrides), and the like, and combinations thereof. Exemplary metals include gold, silver, palladium, platinum, rhodium, copper, nickel, iron, indium, tin, tantalum, and the like, as well as combinations thereof (for example, mixtures, alloys, and compounds of these elements). Preferred metals include silver, gold, copper, platinum, palladium, nickel, and combinations thereof (most preferably, gold).

Preferably, the substrate comprises at least one elemental metal, at least one metal alloy, at least one metal-containing compound, or a combination thereof (more preferably, at least one elemental metal, at least one metal alloy, or a combination thereof; most preferably, at least one elemental metal). As is understood in the art, an elemental metal can comprise relatively small amounts of impurities (for example, up to about 1 percent by weight or more) and still be considered to be an elemental metal.

Coatings of inorganic materials on a physical support (for example, polymer film or glass or silicon wafer) can be of essentially any thickness such as, for example, from about 5 nanometers to about 50 micrometers, from about 10 nanometers to about 10 micrometers, or from about 15 nanometers to about 1000 nanometers. The inorganic material coating can be deposited onto a physical support using any convenient method, for example, sputtering, evaporation, chemical vapor deposition, or chemical solution deposition (including electroless plating).

There are no specific limitations on minimum and maximum thicknesses (or other dimensions) of physical supports for coatings of inorganic material for use in the process of the invention. When the physical support is a polymer film, convenient and useful thickness dimensions can range from about 10 micrometers to about 1 millimeter (preferably, from about 25 micrometers to about 250 micrometers; more preferably, from about 50 micrometers to about 150 micrometers).

Microcontact printing can be carried out by using a relief-patterned stamp or printing plate made of elastomer in combination with a substantially flat substrate in order to transfer to the substrate a pattern of functionalizing molecules according to the relief pattern of the stamp or plate. Alternatively, microcontact printing can be carried out by using a substantially flat stamp or printing plate made of elastomer in combination with a relief-patterned (or structured or microstructured) substrate (for example, a coated polymer film with embossed surface structure on a major surface) in order to transfer to the substrate a pattern of functionalizing molecules according to the relief pattern of the substrate (as described, for example, in U.S. Patent Application Publication No. 2008-0095985-A1 (Frey et al.), the description of which is incorporated herein by reference). The process of the invention is useful for printing in either mode, as will be described in more detail below.

Functionalizing Molecules and Their Preparation

Perfluoropolyether organosulfur compounds useful as functionalizing molecules in carrying out the process of the invention include those that comprise at least one perfluoropolyether segment and at least one organosulfur group. Useful organosulfur groups include those comprising sulfur-containing moieties such as mercapto (—SH), dithio (—S—S—), oxythiocarbonylthio (—O—C(=S)S—), thio (—S—) (such moieties being characteristic of thiol, disulfide, xanthate, and sulfide (including thioether) compounds, respectively), and the like, and combinations thereof.

Preferred perfluoropolyether organosulfur compounds include perfluoropolyether thiol compounds. Such compounds can be prepared by various different known methods including those described in U.S. Pat. No. 6,923,921 (Flynn et al.), the descriptions of which are incorporated herein by reference. Perfluoropolyether thiol compounds can be oxidized by known methods to provide perfluoropolyether disulfide compounds (for example, in the form of dithio-linked dimers of the perfluoropolyether thiol compounds, which can be symmetrical or asymmetrical). Perfluoropolyether sulfides and perfluoropolyether xanthates can be prepared by known methods.

Preferred perfluoropolyether organosulfur compounds include those perfluoropolyether thiols, xanthates, and sulfides that contain only one perfluoropolyether segment, and those perfluoropolyether disulfides that contain only two perfluoropolyether segments (the preferred disulfides being, for example, dimers of the preferred thiols). The perfluoropolyether segment(s) can be linear, branched, cyclic (preferably, alicyclic), or a combination thereof. Preferably, the perfluoropolyether segment is monovalent or divalent and/or the perfluoropolyether segment comprises at least one divalent hexafluoropropyleneoxy group (—CF(CF$_3$)—CF$_2$O—). Preferred perfluoropolyether segments include F[CF(CF$_3$)CF$_2$O]$_a$CF(CF$_3$)—, wherein a has an average value of about 4 to about 20, and —CF(CF$_3$)(OCF$_2$CF(CF$_3$))$_b$OCF$_2$CF$_2$CF$_2$CF$_2$O(CF(CF$_3$)CF$_2$O)$_c$CF(CF$_3$)—, wherein b+c has an average value of about 4 to about 15. Such perfluoropolyether segments can be obtained through the oligomerization of hexafluoropropylene oxide and can be preferred because of their relatively benign environmental properties.

A class of useful perfluoropolyether thiol compounds is that which can be represented by the following general formula (I):

$$R_f\text{-}[Q\text{-}(SH)_x]_y \qquad (I)$$

wherein $R_f$ is a monovalent or divalent perfluoropolyether group; Q is a divalent, trivalent, or tetravalent organic linking group; x is an integer of 1 to 3 (preferably, 1); and y is an integer of 1 or 2 (preferably, 1). Further preferences for $R_f$ and Q include those described below in reference to Formulas II and III.

Preferred perfluoropolyether organosulfur compounds for use as functionalizing molecules in carrying out the process of the invention include those that are amide-linked. Such amide-linked compounds include perfluoropolyether thiol compounds that comprise a perfluoropolyether segment (as described above), at least one mercapto group (—SH), and at least one intervening or interposed divalent carbonylimino moiety (—C(=O)—N(R)—, wherein R is hydrogen or alkyl; preferably, the alkyl group has from one to about four carbon atoms). The divalent carbonylimino moiety can be directly or indirectly (preferably, directly) bonded through its carbon atom to the perfluoropolyether segment and indirectly bonded through its nitrogen atom to the mercapto group. Alternatively, the divalent carbonylimino moiety can be indirectly bonded through its carbon atom to the mercapto group and indirectly bonded through its nitrogen atom to the perfluoropolyether segment. Preferably, the carbonylimino moiety is —C(=O)—NH— (that is, R is hydrogen).

A class of useful amide-linked perfluoropolyether thiol compounds is that which can be represented by the following general formula (II):

$R_f$—[C(=O)—N(R)-Q-(SH)$_x$]$_y$ (II)

wherein $R_f$ is a monovalent or divalent perfluoropolyether group; R is hydrogen or alkyl; Q is a divalent, trivalent, or tetravalent organic linking group; x is an integer of 1 to 3 (preferably, 1); and y is an integer of 1 or 2 (preferably, 1). Preferably, R is hydrogen or an alkyl group having from one to about four carbon atoms (more preferably, hydrogen); and/or Q is a divalent group selected from alkylene, cycloalkylene, arylene, heteroalkylene, and combinations thereof (preferably, alkylene, heteroalkylene, and combinations thereof; more preferably, alkylene), optionally further comprising at least one divalent group selected from carbonyl, carbonyloxy, carbonylthio, carbonylimino, sulfonamido, and combinations thereof (preferably, carbonyl, carbonyloxy, carbonylimino, carbonylthio, and combinations thereof; more preferably, carbonyloxy, carbonylimino, and combinations thereof), and optionally being substituted with at least one moiety selected from alkyl, cycloalkyl, aryl, halo, and combinations thereof.

Preferably, Q has at least about 2 carbon atoms and/or less than or equal to about 30 carbon atoms (more preferably, less than or equal to about 20 carbon atoms; even more preferably, less than or equal to about 10 carbon atoms; most preferably, less than or equal to about 6 carbon atoms). Particularly preferred linking groups, Q, include —CH$_2$CH$_2$—, —CH$_2$CH$_2$CH$_2$—[NH—C(=O)]—CH$_2$CH$_2$CH$_2$—, —CH$_2$CH$_2$CH$_2$—[N(CH$_3$)—C(=O)]—CH$_2$CH$_2$CH$_2$—, —CH$_2$CH$_2$CH$_2$—[N(CH$_3$)—C(=O)]—CH$_2$CH$_2$CH$_2$—S—C(=O)—CH$_2$CH$_2$CH$_2$—, —CH$_2$CH$_2$—[NH—C(=O)]—CH$_2$CH$_2$CH$_2$—, —CH$_2$CH$_2$—[O—C(=O)]—CH$_2$CH$_2$—, —(CH$_2$CH$_2$O)$_2$—[C(=O)]—CH$_2$CH$_2$—, and combinations thereof.

$R_f$ can be linear, branched, cyclic, or a combination thereof and can be saturated or unsaturated. Representative examples of useful $R_f$ groups include, but are not limited to, those that have perfluorinated repeating units selected from —(C$_p$F$_{2p}$)—, —(C$_p$F$_{2p}$O)—, —(CF(Z))—, —(CF(Z)O)—, —(CF(Z)C$_p$F$_{2p}$O)—, —(C$_p$F$_{2p}$CF(Z)O)—, —(CF$_2$CF(Z)O)—, and combinations thereof, wherein p is an integer of 1 to about 10 (preferably, 1 to about 8; more preferably, 1 to about 6; even more preferably, 1 to about 4; most preferably, 1 to about 3); Z is selected from perfluoroalkyl, perfluoroether, perfluoropolyether, and perfluoroalkoxy groups that are linear, branched, cyclic, or a combination thereof and that have less than or equal to about 12 carbon atoms (preferably, less than or equal to about 10 carbon atoms; more preferably, less than or equal to about 8 carbon atoms; even more preferably, less than or equal to about 6 carbon atoms; still more preferably, less than or equal to about 4 carbon atoms; most preferably, less than or equal to about 3 carbon atoms) and/or less than or equal to about 4 oxygen atoms (preferably, less than or equal to about 3 oxygen atoms; more preferably, less than or equal to about 2 oxygen atoms; most preferably, zero or one oxygen atom). In these perfluoropolyether structures, different repeating units can be combined in a block, alternating, or random arrangement to form the $R_f$ group.

When $R_f$ is monovalent, its terminal group can be (C$_p$F$_{2p+1}$)— or (C$_p$F$_{2p-1}$O)—, for example, wherein p is as defined above. Representative examples of useful monovalent $R_f$ groups include, but are not limited to, C$_3$F$_7$O(CF(CF$_3$)CF$_2$O)$_n$CF(CF$_3$)—, C$_3$F$_7$O(CF$_2$CF$_2$CF$_2$O)$_n$CF$_2$CF$_2$—, CF$_3$O(C$_2$F$_4$O)$_n$CF$_2$—, CF$_3$O(CF$_2$O)O$_2$F$_4$O)$_q$CF$_2$ and F(CF$_2$)$_3$O(C$_4$F$_8$O)$_q$(CF$_2$)$_3$— (wherein n has an average value of 0 to about 50, about 1 to about 50, about 3 to about 30, about 3 to about 15, or about 3 to about 10; and q has an average value of 0 to about 50, about 3 to about 30, about 3 to about 15, or about 3 to about 10).

Representative examples of useful divalent $R_f$ groups include, but are not limited to, —CF$_2$O(CF$_2$O)$_n$(C$_2$F$_4$O)$_q$CF$_2$—, —CF$_2$O(C$_2$F$_4$O)$_q$CF$_2$—, —(CF$_2$)$_3$O(C$_4$F$_8$O)$_q$(CF$_2$)$_3$—, and —CF(CF$_3$)(OCF$_2$CF(CF$_3$))$_s$OC$_t$F$_{2t}$O(CF(CF$_3$)CF$_2$O)$_q$CF(CF$_3$)— (wherein n and q are as defined above; s has an average value of 0 to about 50, about 1 to about 50, about 3 to about 30, about 3 to about 15, or about 3 to about 10; the sum of q and s (that is, q+s) has an average value of 0 to about 50 or about 4 to about 40; the sum of q and n (that is, q+n) is greater than 0; and t is an integer of about 2 to about 6).

A preferred class of amide-linked perfluoropolyether thiol compounds for use in the process of the invention is that which can be represented by the following general formula (III):

$R_f'$—(O[CF(CF$_3$)CF$_2$O]$_a$CF(CF$_3$)—[C(=O)—N(R)-Q-(SH)$_x$])$_y$ (III)

wherein $R_f'$ is a linear or branched perfluoroalkyl or perfluoroalkylene group (preferably, having from 1 to about 6 carbon atoms); a has an average value of about 4 to about 20; and R, Q, x, and y are as defined above in reference to general formula II.

Representative examples of useful amide-linked perfluoropolyether thiol compounds include the following, wherein a has an average value of about 4 to about 20 and b+c has an average value of about 4 to about 15:

F[CF(CF$_3$)CF$_2$O]$_a$CF(CF$_3$)—C(=O)—NH—(CH$_2$)$_3$—N(CH$_3$)C(=O)—(CH$_2$)$_3$—SH,

F[CF(CF$_3$)CF$_2$O]$_a$CF(CF$_3$)—C(=O)—NH—(CH$_2$)$_2$SH,

HS—(CH$_2$)$_2$—NH—C(=O)—CF(CF$_3$)(OCF$_2$CF(CF$_3$))$_b$—OCF$_2$CF$_2$CF$_2$O(CF(CF$_3$)CF$_2$O)$_c$—CF(CF$_3$)—C(=O)—NH—(CH$_2$)$_2$SH,

HS—(CH$_2$)$_3$—C(=O)—NH—(CH$_2$)$_2$—NH—C(=O)—CF(CF$_3$)(OCF$_2$CF(CF$_3$))$_b$—OCF$_2$CF$_2$CF$_2$O(CF(CF$_3$)CF$_2$O)$_c$—CF(CF$_3$)—C(=O)—NH—(CH$_2$)$_2$—NHC(=O)—(CH$_2$)$_3$—SH,

F[CF(CF$_3$)CF$_2$O]$_a$CF(CF$_3$)—C(=O)NH—CH$_2$CH$_2$—O—C(=O)—CH$_2$CH$_2$SH,

F[CF(CF$_3$)CF$_2$O]$_a$CF(CF$_3$)—C(=O)NH—(CH$_2$CH$_2$—O)$_2$—C(=O)—CH$_2$CH$_2$SH,

HS—(CH$_2$)$_3$—C(=O)—N(CH$_3$)—(CH$_2$)$_3$—NH—C(=O)—CF(CF$_3$)(OCF$_2$CF(CF$_3$)$_b$—OCF$_2$CF$_2$CF$_2$CF$_2$O(CF(CF$_3$)CF$_2$O)$_c$—CF(CF$_3$)—C(=O)—NH—(CH$_2$)$_3$—N(CH$_3$)C(=O)—(CH$_2$)$_3$—SH, and the like, and combinations thereof.

Such amide-linked perfluoropolyether thiol compounds can be prepared by various different methods. For example, a perfluoropolyether derivative such as a methyl ester, an acid chloride, or an acid fluoride can be reacted with an amine-functional alkanethiol (for example, 2-aminoethanethiol) or a corresponding alkylammonium salt (for example, SH—CH$_2$CH$_2$—NH$_3$$^+$Cl$^−$) under basic conditions (for example, NaOH or KOH) in water. Such methods can provide, however, complex product mixtures comprising relatively low yields of the desired amide-linked perfluoropolyether thiol compound.

Thus, a preferred method of preparation can provide the desired compound in relatively pure form as the major product of the ring opening of a thiolactone with an amine derivative of the corresponding perfluoropolyether. This process comprises (a) providing at least one thiolactone compound (preferably, a thiolactone compound having from about 5 to about 8 ring members; more preferably, from about 5 to about 6 ring members); (b) providing at least one amide-linked perfluoropolyether-substituted, primary or secondary amine compound; and (c) combining the thiolactone compound and the amide-linked perfluoropolyether-substituted, primary or secondary amine compound (preferably, in the presence of at least one tertiary amine).

For example, at least one amide-linked perfluoropolyether-substituted, primary or secondary amine, at least one thiolactone (generally at least a stoichiometric amount relative to the perfluoropolyether amine; preferably, a stoichiometric excess), and, optionally, at least one anhydrous, polar, aprotic solvent (for example, tetrahydrofuran (THF)) can be combined in essentially any order in any suitable reactor (for example, a round bottom flask equipped with a magnetic stir bar, a reflux condenser, and a nitrogen inlet), which can then be stirred and heated to a desired reaction temperature (for example, about 75° C.) under a nitrogen atmosphere. At least one tertiary amine (in at least a catalytic amount) can then be added to the reactor (or can be added continuously or in portions), generally with stirring or agitation of the reactor contents and, preferably, with temperature control.

After completion of tertiary amine addition, or after the reaction has run to completion, the reactor can be cooled and vented, and the reactor contents can be distilled to remove any excess thiolactone and any solvent. If desired, the resulting distilled product optionally can be further purified (for example, prior to spectroscopic analysis) by pouring the product into water and phase-separating the resulting mixture.

Perfluoropolyether-substituted, primary and secondary amine compounds suitable for use in carrying out the preparation process can be prepared by known methods. For example, a perfluoropolyether (as described above) derivative such as a methyl ester can be reacted with a diamine compound having at least one primary amino group (for example, a diaminoalkane having from about 2 to about 6 carbon atoms, such as 1,3-diaminopropane) under a nitrogen atmosphere.

Preferred perfluoropolyether derivatives for reaction with such diamines can be obtained by oligomerization of hexafluoropropylene oxide (HFPO). Such oligomerization provides a carbonyl fluoride derivative, which can be converted to a methyl ester or other derivative by known reactions (for example, those described in U.S. Pat. No. 3,250,808 (Moore et al.), the descriptions of which are incorporated herein by reference). The carbonyl fluoride derivative prepared by such oligomerization is in the form of a mixture of compounds of varying molecular weight having varying degrees of oligomerization (that is, the derivative is not synthesized as a single compound but as a mixture of compounds with different perfluoropolyether groups). Preferably, the mixture has a number average molecular weight of at least about 400 g/mole (more preferably, at least about 800 g/mole; most preferably, at least about 1000 g/mole). For example, the number average molecular weight of the mixture can be from 400 to 10000 g/mole, 800 to 4000 g/mole, or 1000 to 3000 g/mole.

Perfluoropolyether diacyl fluorides can be prepared by the photooxidative polymerization of tetrafluoroethylene (TFE), which results in the formation of perfluoropolyether polyperoxides. The perfluoropolyether polyperoxides can be reduced by physical techniques (for example, thermal or photochemical treatment) or by chemical techniques (for example, reduction with hydrogen in the presence of noble metal catalysts such as platinum or palladium). The reduction breaks the peroxidic perfluoropolyether bonds and can give perfluoropolyethers of lower molecular weight having —COF end groups and randomly-distributed difluoromethyleneoxy and tetrafluoroethyleneoxy moieties. This synthetic method is described in more detail, for example, in U.S. Patent Application Publication No. 2003/0013923 A1 (Marchionni et al.) and in U.S. Pat. No. 5,354,922 (Marchionni et al.), the descriptions of which are incorporated herein by reference.

Perfluoropolyether acyl fluorides can also be prepared by fluoride-catalyzed oligomerization of 1,1,2,2,-tetrafluorooxetane, followed by direct fluorination (as described, for example, in U.S. Pat. Nos. 4,904,417 and 4,845,268 (Ohsaka et al.), the description of which is incorporated herein by reference). These acyl fluorides can be converted to methyl esters by using the above-referenced procedures.

Thiolactone compounds suitable for use in carrying out the preparation process include those that are capable of undergoing a ring-opening reaction when combined with perfluoropolyether-substituted, primary or secondary amines. The thiolactones can be prepared by any of a variety of standard synthetic procedures that are well-known in the art. Some thiolactones (for example, gamma-butyrothiolactone) are also commercially available.

Representative examples of useful thiolactones include gamma-butyrothiolactone, delta-valerothiolactone, and the like, and mixtures thereof. (Mixtures can be used, if desired, but mixtures are generally less preferred due to the resulting production of product mixtures that can require purification.) Gamma-butyrothiolactone is a preferred thiolactone.

Tertiary amines suitable for use in carrying out the preparation process include those that are capable of catalyzing the reaction of thiolactones with perfluoropolyether-substituted, primary or secondary amines. Preferably, the tertiary amines have a relatively low boiling point. The tertiary amines can be prepared by any of a variety of methods that are well-known in the art, and many are commercially available.

Representative examples of useful tertiary amines include trialkylamines such as trimethylamine, triethylamine, and tripropylamine; pyridine; and the like; and combinations thereof. Preferred tertiary amines include trialkylamines (more preferably, trimethylamine, triethylamine, tripropylamine, and combinations thereof; most preferably, triethylamine).

Suitable solvents for use in carrying out the preparation process include anhydrous, polar, aprotic solvents such as glycol ether solvents (for example, glyme, diglyme, triglyme, tetraglyme, and the like, and mixtures thereof), tetrahydrofuran (THF), dimethylformamide, dimethyl sulfoxide, sulfolane, acetonitrile, and the like, and mixtures thereof. Preferred solvents include THF, glyme, diglyme, triglyme, tetraglyme, dimethylformamide, and mixtures thereof; with THF, glyme, diglyme, dimethylformamide, and mixtures thereof being more preferred and THF most preferred.

Patterning Composition

Patterning compositions useful in carrying out the process of the invention comprise at least one functionalizing molecule, as described above. Optionally, but preferably, the compositions can further comprise at least one solvent. Useful solvents include those in which the functionalizing molecules are relatively highly soluble (for example, at concentrations greater than about 1 millimolar (mM) or even greater than about 10 millimolar (mM)). It is also preferable that the solvents do not significantly react with the functionalizing molecules. Preferably, patterning compositions that comprise solvent can remain stable for extended periods of time (for example, for months or even years without precipitation, decomposition, or other reaction involving the functionalizing molecules).

Suitable solvents for use in the patterning compositions include alcohols, ketones, aromatic compounds, heterocyclic compounds, fluorinated solvents, and the like, and combinations thereof. Other useful solvents include dimethylformamide, acetonitrile, dimethylacetamide, dimethylsulfoxide, ethyl acetate, tetrahydrofuran (THF), methyl t-butyl ether (MTBE), and the like, and combinations thereof. Preferred solvents include tetrahydrofuran, methyl t-butyl ether, ethanol, isopropanol, and combinations thereof.

Although microcontact printing has been carried out using neat organosulfur compounds, the delivery of organosulfur compounds to a stamp can be achieved more uniformly, and with less stamp swelling in the case of polydimethylsiloxane (PDMS) stamps for example, if delivered from a solvent-based composition. Preferred solvents have tailored drying behavior for rapid and uniform deposition of the organosulfur compound on or within the stamp. Preferred solvents have a boiling point between about 50° C. and about 100° C. at atmospheric pressure (more preferably, between about 55° C. and about 85° C.; most preferably, between about 55° C. and about 77° C.).

Such solvents are preferably compatible with PDMS (that is, they do not excessively swell PDMS), which is the most commonly used material for microcontact printing. Some common solvents such as, for example, toluene and diethyl ether can swell PDMS too much to be used effectively in microcontact printing. In microcontact printing, swelling of the PDMS stamp can lead to distortion of the patterned features and poor pattern fidelity. Depending on the inking approach, excessive swelling can also present significant challenges in providing mechanical support to the stamp.

Preferred solvents therefore have a relatively low PDMS swelling ratio, $D/D_0$, wherein D is the length of a piece of PDMS in a solvent, $D_0$ is the length of the same piece of PDMS when dry, and the PDMS is Sylgard™ 184 PDMS, commercially obtainable from Dow Corning, Midland, Mich. A procedure for measuring swelling ratio is described by Lee et al. in "Solvent Compatibility of Poly(dimethylsiloxane)-Based Microfluidic Devices, *Analytical Chemistry* Vol. 75, pp. 6544-6554 (2003), the description of which is incorporated herein by reference. Preferred solvents have a PDMS swelling ratio of less than about 1.25 (more preferably, less than about 1.10; most preferably, 1.06 or less).

Preferred solvents for microcontact printing have a relative polarity of less than about 0.7. Relative polarity is the normalized transition energy for the longest wavelength solvatochromic absorption band of the pyridinium-N-phenoxide betaine dye, as described in detail in *Solvents and Solvent Effects in Organic Chemistry*, Second Edition, C. Reichardt, VCH Verlagsgesellschaft mbH, Germany (1988). The normalization creates a unitless relative polarity scale bounded by tetramethylsilane at 0.000 and water at 1.000. Values of relative polarity for most solvents can be found in the aforementioned volume by Reichardt.

Ketones and the like can be suitable solvents for microcontact printing. Preferred solvents include, for example, ethanol, acetone, methyl ethyl ketone, ethyl acetate, and the like, and combinations thereof. Acetone is a particularly preferred solvent.

Preferably, when solvent is used, the functionalizing molecules are present in the solvent at a concentration less than their solubility limit. Useful compositions also include, however, those in which the functionalizing molecules are not completely dissolved in the solvent. The functionalizing molecules can be present in the solvent in a total concentration (that is, the molar concentration of all the functionalizing molecules taken in aggregate) of at least about 0.1 mM. Preferably, the total concentration of functionalizing molecules ranges up to any total concentration in which the patterning composition still consists of essentially a single phase. The functionalizing molecules can be present in total concentrations of at least about 1 mM, at least about 2 mM, at least about 5 mM, or even at least about 10 mM.

The patterning compositions preferably contain essentially no solid particles of the functionalizing molecules or solid particles derived from the functionalizing molecules (for example, typically being present at a level of less than about 10 percent by weight of the total weight of functionalizing molecules; preferably, less than about 5 percent; more preferably, less than about 1 percent). Most preferably, the patterning compositions do not contain any (that is, zero percent) such solid particles (for example, undissolved particles, reprecipitated particles, or solid reaction products in the form of crystals, gelatinous precipitates, or flocs of oxidation products).

The patterning compositions can comprise relatively small amounts of common additives (for example, stabilizers or desiccants), if desired. Examples of useful stabilizers include those described, for example, by Srinivas et al. in "Bioanalytical considerations for compounds containing free sulfhydryl groups," *Biomedical Chromotography* Vol. 17, pp. 285-291 (2003)). Preferably, additives such as stabilizers can be included in the compositions in a sufficiently small amount so as to not significantly interfere with the ability of the perfluoropolyether organosulfur compound(s) to functionalize the substrate surface.

A preferred patterning composition comprises (a) at least one amide-linked perfluoropolyether organosulfur compound (preferably, at least one amide-linked perfluoropolyether organosulfur compound selected from amide-linked perfluoropolyether thiol compounds, amide-linked perfluoropolyether disulfide compounds, amide-linked perfluoropolyether xanthate compounds, amide-linked perfluoropolyether sulfide compounds, and combinations thereof; more preferably, at least one amide-linked perfluoropolyether organosulfur compound selected from amide-linked perfluoropolyether thiol compounds, amide-linked perfluoropolyether disulfide compounds, and combinations thereof; most preferably, at least one amide-linked perfluoropolyether thiol compound); and (b) at least one solvent. Preferably, the amide-linked perfluoropolyether organosulfur compounds comprise at least two carbonylimino moieties or comprise at least one carbonylimino moiety and at least one carbonyloxy moiety.

Application of Patterning Composition

The patterning composition can be applied to the major surface of the substrate in essentially any manner that can form at least one functionalized region and at least one unfunctionalized region of the major surface. This can involve application to only a portion of the surface or, alternatively, application to essentially all of the surface followed by selective removal (for example, by patterned degradation using a pattern of ultraviolet (UV) light, an electron beam, bombarding atoms, the probe of a scanning probe microscope (scanning tunneling microscope or atomic force microscope), or the like, or a combination thereof) from a portion thereof. Useful application methods include printing and coating methods such as flexographic printing, ink jet printing, gravure printing, dip coating, spin coating, spray coating, and the like, and combinations thereof.

Preferably, the application method is a method that can provide a functionalized region that comprises a self-assembled monolayer (SAM) of the functionalizing molecule. Such methods include adsorption from solution by immersion of all or a portion of the substrate in the solution, as well as methods such as microcontact printing, ink jet printing, topographically directed assembly, and the like, and combinations thereof. Microcontact printing is a preferred method of application of the patterning composition to the surface of the substrate.

The patterning composition can be microcontact printed to provide patterned functionalizing molecules (including patterned SAMs) that are useful, for example, as etch resists, templates for crystallization, and model surfaces for biological studies. As is known in the art, such printing can include a displacement reaction that results in removal or modification of an atom or functional group in the functionalizing molecule (for example, conversion of a thiol (R—SH compound) to a thiolate (R—S-M) monolayer when the monolayer is formed on a metal (M), for example gold, as described, for example, by Love et al. in "Self-Assembled Monolayers of Thiolates on Metals as a Form of Nanotechnology," *Chemical Reviews* Vol. 105, pp. 1103-1169 (2005)). Thus, the resulting printed pattern can comprise compounds or molecules that are chemically different from the functionalizing molecules in the patterning composition.

Microcontact printing typically utilizes a relief-patterned elastomeric stamp. Useful elastomers for forming the stamp include silicones, polyurethanes, ethylene propylene diene M-class (EPDM) rubbers, as well as the range of existing commercially available flexographic printing plate materials (for example, commercially available from E. I. du Pont de Nemours and Company, Wilmington, Del., under the trade name Cyrel™). The stamp can be made from a composite material (for example, one of the aforementioned elastomers combined with a woven or non-woven fibrous reinforcement).

Polydimethylsiloxane (PDMS) is particularly useful as a stamp material, as it is elastomeric and has a low surface energy (which makes it easy to remove the stamp from most substrates). PDMS is also commercially available. A useful commercially available formulation is Sylgard™ 184 PDMS (Dow Corning, Midland, Mich.). PDMS stamps can be formed, for example, by dispensing an uncrosslinked PDMS polymer into or against a patterned mold, followed by curing. The patterned features can be, for example, millimeter-sized, micrometer-sized, nanometer-sized, or a combination thereof.

Particularly useful stamp materials for use with the patterning compositions described herein, including the perfluoropolyether organosulfur compounds and in particular the perfluoropolyether thiols and amide-linked perfluoropolyether thiols, include perfluoropolyether elastomers having, for example, hexafluoropropylene oxide units or tetrafluoroethylene oxide units. Suitable materials for preparing perfluoropolyether elastomers and stamps based thereon include reactive perfluoropolyether-containing compounds that are described, for example, in U.S. Pat. No. 3,810,874 (Mitsch et al.) and by J. P. Rolland et al. in "High-Resolution Soft Lithography: Enabling Materials for Nanotechnologies," Angewandte Chemie 43, 5796 (2004). Some such compounds can be obtained commercially, for example, from Sartomer Company of Exton, Pa., under the trade designation CN 4000.

The stamp can be "inked" with the patterning composition using methods known in the art (for example, the methods described by Libioulle et al. in "Contact-Inking Stamps for Microcontact Printing of Alkanethiols on Gold," *Langmuir* Vol. 15, pp. 300-304 (1999)). In one approach, an applicator (for example, a cotton swab or a foam applicator) impregnated with the patterning composition can be rubbed across the relief-patterned surface of the stamp, followed by drying of solvent from the stamp surface. In another approach, the stamp can be pressed against an "ink pad" impregnated with the patterning composition, the ink pad optionally being a PDMS slab. In another approach, the stamp can be charged with patterning composition from its back side, relative to the printing surface. In the latter approach, the functionalizing molecule diffuses through the stamp to reach the relief-patterned face for printing. Alternatively, the relief-patterned printing face of the stamp can be immersed in the patterning composition, followed by withdrawal and drying ("immersive inking"). All of the above described methods of inking render the relief-patterned stamp surface inked, yielding an "inked surface."

The inked stamp can be used to transfer a pattern of the functionalizing molecule to the surface of the substrate to form at least one functionalized region and at least one unfunctionalized region of the surface. When the inked surface of the stamp comprises a relief pattern, the inked surface can be contacted to a surface of a substrate that is essentially flat in order to transfer a pattern of the functionalizing molecule to the surface of the substrate, wherein the pattern of the functionalizing molecule is essentially the same as the pattern of raised features in the relief pattern of the inked surface of the stamp. In such a process, the pattern is said to be transferred according to the relief pattern of the inked surface of the stamp.

When the inked surface of the stamp (or, alternatively, a printing plate) is essentially flat, the inked surface can be contacted to a surface of a substrate that comprises a relief pattern in order to transfer a pattern of the functionalizing molecule to the surface of the substrate, wherein the pattern of the functionalizing molecule is essentially the same as the pattern of raised features in the relief pattern of the surface of the substrate. In such a process, the pattern is said to be transferred according to the relief pattern of the surface of the substrate. U.S. Pat. No. 6,518,168 (Clem et al.), for example, describes this "reverse" microcontact printing process.

When the inked surface of the stamp comprises a first relief pattern, the inked surface can be contacted to a surface of a substrate that comprises a second relief pattern in order to transfer a pattern of the functionalizing molecule that is defined by the regions of contact between the raised features of the first relief pattern and the raised features of the second relief pattern (that is, the intersection of relief patterns). In such a process, the pattern of the functionalizing molecule is said to be transferred according to both of the relief patterns.

Preferably, for the achievement of manufacturing efficiency in the use of the immersive inking approach, it can be desired that the inking time (that is, the time the stamp is in contact with the patterning composition) be as short as possible, while still yielding an inked stamp with adequate printing performance. It can also be desirable that the drying time (prior to contact with the surface of the substrate) be as short as possible. These factors drive a desire for patterning compositions that can be stable at high concentration and that can be dried rapidly on the stamp surface.

Preferably, the solvent of the patterning composition can be selected so as to evaporate relatively rapidly from the stamp surface, as this can also be helpful for achieving a relatively uniform distribution of the functionalizing molecules on or within the stamp with a minimum of time and application of forced air. For immersive inking, it can be preferred that the inking time is less than about 60 seconds, more preferably less than about 45 seconds, yet more preferably less than about 30seconds, and even more preferably less than about 15 seconds.

After withdrawal and drying, the inked stamp can be placed in contact with the surface of the substrate such that contact is made with the raised regions of the relief-patterned surface of the stamp. The functionalizing molecules can diffuse from the stamp onto the surface of the substrate where they can form SAMs.

The printing time (that is, the duration of contact between the stamp and the substrate) can vary, depending upon factors including, for example, the concentration of the patterning composition and the pressure applied to the stamp. In some embodiments, the print time can be less than 1 minute (preferably, less than about 30 seconds; more preferably, less than about 10 seconds; most preferably, less than about 5 seconds).

Etching

The resulting functionalized region(s) of the surface of the substrate (preferably, comprising a patterned SAM formed by the functionalizing molecules of the patterning composition) can be used, for example, as a resist that protects the underlying substrate surface during a subsequent patterning step. For example, the functionalized region(s) can serve as an etch mask. As an etch mask, the functionalized region(s) of the substrate surface (for example, the surface of a metal coating on a polymeric film) can be protected against the action of an etchant, while the unfunctionalized region(s) of the surface of the substrate are not protected, allowing selective removal of material (for example, metal) in the unfunctionalized region(s).

Etching of the substrate can be carried out by essentially any known or hereafter-developed method that can etch at least a portion of the unfunctionalized region of the particular substrate that is being utilized. Such methods include the use of chemical etchants including gaseous etchants (to provide a "dry etch"), etchant solutions (to provide a "wet etch"), and the like, and combinations thereof. Dry etching can be preferred for its controllability, but wet etching is generally preferred for reasons of economy and ease of removal of etching by-products.

Preferably, the etching of the unfunctionalized region is selective or, in other words, without significant etching of the functionalized region (for example, etching of less than about 50 percent of the amount etched from the unfunctionalized region per unit area; preferably, less than about 25 percent; more preferably, less than about 10 percent; most preferably, less than about 5 percent). The amount of material etched from a functionalized region or an unfunctionalized region, complementary to the amount of material that remains after etching, can be determined by using known methods (for example, methods based on transmitted light attenuation, profilometry, mass analysis, or the like).

Useful chemical etching baths can be prepared by dissolving etchant species in water or a non-aqueous solvent (for example, with agitation or stirring, control of pH, control of temperature, and/or replenishment of etchant species upon their consumption, according to the nature of the etchant). Contact between the etchant and the substrate can be achieved in essentially any effective manner.

For example, the substrate can be immersed in the bath for a period of time (which can vary according to the nature of the substrate and/or the etchant) or, alternatively, the etchant solution can be sprayed over the substrate. In some wet etching processes, it can be useful to agitate the etch bath, the substrate, or both during etching (for example, by stirring, flowing, and/or ultrasonically activating the etch bath, and/or by shaking, translating, rotating, and/or vibrating the substrate).

Useful chemical etchants include those that have been used for etching, for example, metals such as gold, silver, copper, palladium, platinum, and the like (for example, ferric chloride-based, cyanide/oxygen-based, ferrocyanide/ferricyanide-based, thiourea-based, and potassium iodide/iodine-based ($KI/I_2$; "tri-iodide") etchant systems, and the like, and combinations thereof). Some wet chemical etchants are commercially available (for example, from the Transene Company, Inc., Danvers, Mass.).

Potassium iodide/iodine-based etchants (one example of a tri-iodide etchant system) can be preferred in the etch patterning of gold or silver, as they are commercially available and offer a compelling combination of stability (for example, for periods of weeks), capacity (for example, greater than about 20 grams of substrate removed per liter of etchant), speed (for example, etch rates of about 25-660 nanometers per minute), and safety (see, for example, "Wet etching of gold films compatible with high Tc superconducting thin films" by W. Eidelloth and R. L. Sandstrom in Applied Physics Letters 59(13), 1632 (1991)). Other useful tri-iodide etchant systems include aqueous solutions including ammonium iodide ($NH_4I$) and iodine ($I_2$) (see, for example, "Visualization of DNA hybridization on gold thin film by utilizing the resistance effect of DNA monolayer" by T. Masuda et al. in Sensors and Actuators B 105, 556 (2005)).

As is known in the art, in simple etchant solutions formed by the combination of potassium iodide salt and iodine beads (as starting materials) with water, additional iodine-containing species can be formed and can exist in chemical equilibrium with the starting materials or soluble constituents of the starting materials. The equilibrium behavior of $I^-$, $I_2$, and $I_3^-$ species is well-known, wherein tri-iodide species are formed from iodide salt and iodine starting materials (see, for example, "Thermodynamics of Iodine Solubility and Triiodide Ion Formation in Water and in Deuterium Oxide," by R. W. Ramette and R. W. Sandford, Jr., in Journal of the American Chemical Society 87(22), 5001 (1965)).

Despite the known and useful etching behavior of tri-iodide etchant systems, including for the etching of gold, their combination with printed masks of functionalizing molecules (for example alkylthiol molecules) for the patterning of metals (for example gold) has been challenging (see, for example, "Thiosulfate- and Thiosulfonate-Based Etchants for the Patterning of Gold Using Microcontact Printing" by D. Burdinski and M. H. Blees in Chemistry of Materials 19, 3933 (2007)). The functionalizing molecules disclosed herein for use in the process of the invention, however, can be printed in fine-scale patterns (for example by microcontact printing) and can exhibit at least adequate resistance to serve as an etch mask for tri-iodide based etchants.

For use in carrying out the process of the invention, the tri-iodide etchant starting material(s) can be combined with solvent at essentially any concentration that can provide the desired etching properties. For example, tri-iodide etchants for use in etching substrates comprising gold can be prepared by combining an iodide salt (for example, potassium, sodium, or ammonium iodide), iodine ($I_2$), and water at preferred concentration ranges for the salt and the iodine of about 0.5-5 and about 2-20 percent by weight, respectively. A combination based on the lower ends of these ranges can be useful for etching gold at a slower rate (for example, less than about 25 nanometers per minute), while a combination based on the higher ends of these ranges can be useful for etching gold at a faster rate (for example, greater than about 600 nanometers per minute).

Preferred tri-iodide etchant formulations for use in etching substrates comprising gold include iodine at a weight percent level that is from about 2 to about 5 times the weight percent level of the iodide salt. In terms of molar concentrations, these preferred ranges for the iodide salt and the iodine, as batched in the formulation of the etchant, are from about 0.02 M to about 0.25 M and from about 0.1 M to about 1.5 M, respectively. As is known, the equilibrium amongst $I^-$, $I_2$, and $I_3^-$ can lead to changes in the actual concentration of "iodide species" from their batched levels.

In a preferred embodiment of the process of the invention, the application of the patterning composition (preferably, the above-described preferred patterning composition, or the corresponding composition without solvent) to the substrate (preferably, a substrate comprising gold) is carried out by microcontact printing, and the etching of the substrate is carried out by chemical etching using a tri-iodide (for example, a potassium iodide/iodine-based) etchant system.

Optional Process Steps

If desired, substrate surfaces can be treated by any of a number of different processes prior to application of the patterning composition. Examples of optional treatment processes include ultraviolet light-ozone cleaning, oxygen plasma cleaning, solvent degreasing, high-pressure washing, and detergent-based cleaning.

Electroless or electrolytic overplating of the substrate can be carried out, if desired, following removal of the patterning composition. This can provide for amplification of the electrical conductance of metallic features in the resulting pattern by adding current-carrying material selectively to the features. Such additive post-processing can be preferred in some applications over originally etch-patterning a thicker metal deposit (for example, due to fewer technical difficulties or lower cost).

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Preparation of Functionalizing Molecules

Materials

Gamma-butyrothiolactone, mercaptoethanolammonium hydrochloride, triethylamine, N-methyl-1,3-diaminopropane, monoethanolamine, ethylenediamine, diisopropylethylamine, and methanesulfonyl chloride were obtained from Aldrich Chemical Company, Milwaukee, Wis. All solvents were standard reagent grade obtained from commercial sources and were used without further purification unless specified otherwise.

Unless otherwise noted, "HFPO—" refers to the monovalent end group $F(CF(CF_3)CF_2O)_aCF(CF_3)$— of the methyl ester $F(CF(CF_3)CF_2O)_aCF(CF_3)C(=O)OCH_3$, wherein "a" averaged about 6.7, and the methyl ester had an average molecular weight of about 1,211 g/mole. This methyl ester was prepared by essentially the method described in U.S. Pat. No. 3,250,808 (Moore et al.), the description of this method being incorporated herein by reference, with purification by fractional distillation. This methyl ester was converted to the amidol HFPO—$C(=O)NHCH_2CH_2OH$ by treatment with monoethanolamine, essentially as described in U.S. Patent Application Publication No. 2005/0250921 (Qiu et al) on pages 6 and 7 under the procedure for FC-4.

The dimethyl ester $CH_3O(O=)C$—$CF(CF_3)(OCF(CF_3)CF_2)_bOCF_2CF_2CF_2CF_2O$—$(CF_2CF(CF_3)O)_cCF(CF_3)$—$C(=O)OCH_3$, wherein b+c averaged about 8.4, was prepared using $FC(=O)CF_2CF_2C(=O)F$ as a starting material, essentially according to the method described in U.S. Pat. No. 3,250,807 (Fritz et al.), which provided the corresponding oligomeric bis-acid fluoride, followed by methanolysis and purification by removal of lower boiling materials by fractional distillation, essentially as described in U.S. Pat. No. 6,923,921 (Flynn et. al.), the descriptions of both methods being incorporated herein by reference. Unless otherwise noted, "—HFPO—" refers to the divalent oligomer —$CF(CF_3)(OCF(CF_3)CF_2)_bOCF_2CF_2CF_2CF_2O(CF_2CF(CF_3)O)_cCF(CF_3)$—, and thus the above-described dimethyl ester can be termed alpha, omega-HFPO—$[C(=O)OCH_3]_2$.

HFPO—$C(=O)NH$—$CH_2CH_2CH_2$—$N(CH_3)H$ was prepared essentially as described in U.S. Pat. No. 7,335,786 (Iyer et al), Preparative Example 1.

HFPO[—$C(=O)NH$—$CH_2CH_2$—$NH_2]_2$ was prepared essentially as described in U.S. Pat. No. 7,335,786 (Iyer et al), Preparative Example 3.

HFPO—$C(=O)NHCH_2CH_2OCH_2CH_2OH$ was prepared by the following procedure: A 500 mL round bottom flask equipped with magnetic stir bar, oil bath, reflux condenser, and nitrogen inlet was charged with HFPO—$C(=O)OCH_3$ (70 g, 0.0537 mole) and $NH_2$—$CH_2CH_2$—$O$—$CH_2CH_2$—$OH$ (5.65 g, 1 molar equivalent) under a nitrogen atmosphere. The resulting mixture was allowed to stir at 75° C. for 16 hours. A sample of the mixture was then analyzed by infrared spectroscopy (IR) and proton ($^1H$) NMR, and the resulting spectral data confirmed formation of the desired product. The mixture was washed with brine (5×50 mL), and extracted with methyl t-butyl ether (MTBE). The resulting extract was dried over $MgSO_4$, filtered, stripped of solvent using rotary evaporation, and then kept under vacuum for 12 hours at room temperature.

$C_4F_8SO_2N(CH_3)CH_2CH_2OH$ (MeFBSE) and HFE-7100 (methyl perfluorobutyl ether) were obtained from 3M Company, St. Paul, Minn.

$C_4F_9SO_2$—$N(CH_3)CH_2CH_2$—$NH_2$ was prepared by the following procedure: N-Methylnonafluorobutanesulfonamide (626 g, 2 moles, 3M Company, St. Paul, Minn.), 2-ethyl-2-oxazoline (198 g, 2 moles, Alfa Aesar, Ward Hill, Mass.), and sodium carbonate (17 g, 0.16 mole, EMD Chemicals, Gibbstown, N.J.) were combined and heated for 16 hours at 140° C. to form N-(2-(N-methylnonafluorobutanesulfonamido)ethyl)propionamide. This amide was twice extracted with 250 mL deionized water, heated for 18 hours at 100° C. with a mixture of 250 mL concentrated hydrochloric acid and 100 mL deionized water, extracted with 925 mL of 24 weight percent aqueous sodium hydroxide solution, extracted with 250 mL 10 weight percent aqueous sodium hydroxide solution, and distilled to provide N-(2-aminoethyl)-N-methylnonafluorobutanesulfonamide (538 g; 75 percent recovery; 94 percent pure by gas chromatography (GC); distilled at 104-109° C. under 2 mm Hg pressure).

Synthesis of HFPO—C(=O)—NH—$(CH_2)_3$—$N(CH_3)$C(=O)—$(CH_2)_3$—SH (Molecule No. 1)

A 50 mL round bottom flask equipped with magnetic stir bar, oil bath, reflux condenser, and nitrogen inlet was charged with HFPO—C(=O)NH—$CH_2CH_2CH_2$—$N(CH_3)H$ (5 g, 0.0039 mole), gamma-butyrothiolactone (4.03 g, 10 molar equivalents) and tetrahydrofuran (THF) (25 g) under a nitrogen atmosphere. The resulting mixture was turbid and allowed to stir at room temperature for 5 minutes. Triethylamine (3.985 g, 10 molar equivalents) was added to the mixture dropwise by syringe at room temperature. The mixture became clear after the addition of triethylamine and was allowed to stir at 75° C. for 16 hours. Excess unreacted gamma-butyrothiolactone was distilled out under vacuum, and the resulting mixture was poured into ice water. The resulting organic phase was extracted with HFE-7100, dried over $MgSO_4$, and filtered. Removal of solvent under vacuum left a paste that was analyzed by nuclear magnetic resonance spectroscopy (NMR) and gas chromatography-mass spectrometry (GC-MS). The resulting spectral data were consistent with formation of the desired product.

Synthesis of HFPO—C(=O)—NH—$CH_2CH_2$—SH (Molecule No. 2)

A 500 mL round bottom flask equipped with magnetic stir bar, oil bath, reflux condenser, and nitrogen inlet was charged with HFPO—C(=O)$OCH_3$ (100 g, 0.0761035 mole) and $NH_2$—$CH_2CH_2$—SH (7.05 g, 1.2 molar equivalents) under a nitrogen atmosphere. The resulting mixture was allowed to stir at 75° C. for 16 hours. A sample of the mixture was then analyzed by infrared spectroscopy (IR) and proton ($^1$H) NMR, and the resulting spectral data confirmed formation of the desired product. The mixture was washed with $CH_2Cl_2$ (5×50 mL), and the $CH_2Cl_2$ washings were combined, dried over $MgSO_4$, filtered, and the resulting product was stripped of solvent under vacuum for 12 hours at room temperature.

Synthesis of HFPO—[C(=O)—NH—$(CH_2)_2SH]_2$ (Molecule No. 3)

A 500 mL round bottom flask equipped with magnetic stir bar, oil bath, reflux condenser, and nitrogen inlet was charged with alpha, omega-HFPO—[C(=O)$OCH_3]_2$ (50 g, 0.0325 mole) and $NH_2$—$CH_2CH_2$—SH (6.035 g, 2.4 molar equivalents) under a nitrogen atmosphere. The resulting mixture was allowed to stir at 75° C. for 16 hours. A sample of the mixture was analyzed by IR and $^1$H NMR, and the resulting spectral data confirmed formation of the desired product. The mixture was extracted with $CH_2Cl_2$ (5×50 mL), and the combined $CH_2Cl_2$ extracts were dried over $MgSO_4$, filtered, and stripped of solvent under vacuum for 12 hours.

Synthesis of HFPO[—C(=O)—NH—$(CH_2)_2$—NHC(=O)—$(CH_2)_3$—$SH]_2$ (Molecule No. 4)

A 250 mL round bottom flask equipped with magnetic stir bar, reflux condenser, and nitrogen inlet was charged with HFPO[—C(=O)NH—$CH_2CH_2$—$NH_2]_2$ (10 g, 0.00628 mole), gamma-butyrothiolactone (6.4 g, 20 molar equivalents), and THF (80 g) under a nitrogen atmosphere. The resulting mixture was turbid and allowed to stir at room temperature for 5 minutes. Triethylamine (6.3 g, 20 molar equivalents) was added to the mixture dropwise by syringe at room temperature. The mixture became clear after the addition of triethylamine and was allowed to stir at 75° C. for 16 hours. Excess unreacted gamma-butyrothiolactone was distilled out, and the resulting mixture was poured into ice water. The resulting organic phase was extracted into HFE-7100, dried over $MgSO_4$, filtered, and solvent stripped under vacuum at room temperature. The resulting paste was analyzed by NMR and GC-MS, and the resulting spectral data confirmed formation of the desired product.

Synthesis of HFPO—C(=O)—NH—$CH_2CH_2$—O—C(=O)—$CH_2CH_2$—SH (Molecule No. 5)

A 500 mL round bottom flask equipped with magnetic stir bar, oil bath, Dean-Stark apparatus, reflux condenser, and nitrogen inlet was charged with HFPO—C(=O)$NHCH_2CH_2OH$ (100 g, 0.06463 mole), HO(O=)C—$CH_2CH_2$—SH (8.23 g, 0.077 mole), p-toluenesulfonic acid (13 g), and toluene (600 g) under a nitrogen atmosphere. The resulting mixture was allowed to reflux and stir for 16 hours. The mixture was cooled and filtered, and solvent was removed from the mixture by rotary evaporation. The resulting residue was washed with water (500 mL×6 times), and the resulting organic portion was dissolved in methyl t-butyl ether (MTBE) (500 mL), dried over $MgSO_4$, filtered, and stripped by rotary evaporation to provide the desired product in 73 percent yield.

Synthesis of HFPO—C(=O)—NH—$(CH_2CH_2$—$O)_2$—C(=O)—$CH_2CH_2$—SH (Molecule No. 6)

A 500 mL round bottom flask equipped with magnetic stir bar, oil bath, Dean-Stark apparatus, reflux condenser, and nitrogen inlet was charged with HFPO—C(=O)$NHCH_2CH_2OCH_2CH_2OH$ (100 g, 0.0727 mole), HO(O=)C—$CH_2CH_2$—SH (9.65 g, 0.090 mole), p-toluenesulfonic acid (13 g), and toluene (600 g) under a nitrogen atmosphere. The resulting mixture was allowed to reflux and stir for 16 hours. The mixture was cooled and filtered, and solvent was removed from the mixture by rotary evaporation. The resulting residue was washed with water (500 mL×6 times), and the resulting organic portion was dissolved in MTBE (500 mL), dried over $MgSO_4$, filtered, and solvent stripped by rotary evaporation to provide the desired product in 82 percent yield.

Synthesis of $C_4F_9SO_2N(CH_3)CH_2CH_2NH$—C(=O)—$CH_2CH_2CH_2SH$ (Comparative Molecule C-1)

A 250 mL round bottom flask equipped with magnetic stir bar, oil bath, reflux condenser, and nitrogen inlet was charged with $C_4F_9SO_2N(CH_3)CH_2CH_2NH_2$ (10 g, 0.028 mole), gamma-butyrothiolactone (28.083 g, 10 molar equivalents), and THF (75 g) under a nitrogen atmosphere. The resulting mixture was turbid and was allowed to stir at room temperature for 5 minutes. Triethylamine (28.3 g, 10 molar equivalents) was added to the mixture dropwise by syringe at room temperature. The mixture became clear after the addition of triethylamine and was allowed to stir at 75° C. for 16 hours. Excess gamma-butyrothiolactone was distilled out, and the resulting mixture was poured into ice water. The resulting organic phase was extracted in $CH_2Cl_2$, the washings were combined and dried over $MgSO_4$, and solvent was stripped under vacuum. The resulting product was analyzed by NMR and GC-MS, and the resulting spectral data confirmed formation of the desired product.

Synthesis of $C_4F_9SO_2N(CH_3)CH_2CH_2$—SH (Comparative Molecule C-2)

A mixture of 35.7 g (0.1 mole) MeFBSE, 14.0 g diisopropylethylamine, and 200 mL dichloromethane was treated dropwise with 11.5 g methanesulfonyl chloride in 20 mL dichloromethane. After washing the treated mixture with water and drying over $MgSO_4$, solvent was removed from the mixture to leave 50.4 g white solid. The solid (8.7 g) was heated with 2.2 g thiourea in 10 mL glyme overnight at about 60° C., causing a precipitate to form. Ethyl ether was added to the precipitate-containing glyme, and the resulting mixture was filtered to provide 5.0 g isothiouronium salt. The salt was heated in dilute NaOH, and the resulting solution was acidified, preciptating the thiol as a white solid. GC/MS data on the solid confirmed formation of the desired product.

Synthesis of $C_4F_9SO_2N(CH_3)CH_2CH_2OC(=O)CH_2CH_2SH$ (Comparative Molecule C-3)

A mixture of MeFBSEA (10 g, 0.028 mole), SH—$CH_2CH_2$—COOH (3.56 g, 0.0336 mole), and p-toluenesulfonic acid (PTSA) (1 g, 10 weight percent based on starting alcohol) was refluxed in toluene. Reaction of the mixture was monitored by IR, and, after the disappearance of an alcohol peak, the toluene was distilled out and the resulting product was added into brine. The resulting organic portion was extracted with dichloromethane, washed with water, and dried over $MgSO_4$.

Synthesis of Comparative Molecules C-4, C-5, and C-6

These functionalizing molecules (having the chemical structures shown in Table 1 below) were synthesized essentially by the method described by R. S. Clegg and J. E. Hutchison in "Control of Monolayer Assembly Structure by Hydrogen Bonding Rather Than by Adsorbate-Substrate Templating," Journal of the American Chemical Society 121, 5319 (1999).

Comparative Molecules C-7 and C-8

These molecules (having the chemical structures shown in Table 1 below) were purchased from Aldrich Chemical Company, Milwaukee, Wis., as Catalog Nos. 08686 (1H,1H,2H, 2H-perfluoro-1-decanethiol) and 674516 (1-hexadecanethiol), respectively.

Examples 1-6 and Comparative Examples C-1-C-8:
Application by Immersion

Preparation of Patterning Compositions

The various functionalizing molecules shown in Table 1 below were used to prepare a series of patterning compositions by combining each molecule with solvent (either ethanol (EtOH) or tetrahydrofuran (THF)) in the proportions shown in Table 1.

TABLE 1

| Example/Molecule No. | Molecule Structure | Patterning Composition |
|---|---|---|
| 1 | HFPO-C(=O)-NH-(CH2)3-N(CH3)-C(=O)-(CH2)3-S-H | 2.2 g in 180 g EtOH |
| 2 | HFPO-C(=O)-NH-CH2CH2-S-H | 3.9 g in 200 g EtOH |
| C-1 | $C_4F_9SO_2$-N(CH3)-CH2CH2-NH-C(=O)-(CH2)3-S-H | 4 g in 180 g EtOH |
| 3 | [HFPO-C(=O)-NH-CH2CH2-S-H]$_n$, n = 2 | 4 g in 180 g EtOH |
| C-2 | $C_4F_9SO_2$-N(CH3)-CH2CH2-SH | 2 g in 200 g THF |
| 4 | [HFPO-C(=O)-NH-CH2CH2-NH-C(=O)-(CH2)3-S-H]$_n$, n = 2 | 4 g in 180 g EtOH |

TABLE 1-continued

| Example/Molecule No. | Molecule Structure | Patterning Composition |
|---|---|---|
| 5 | HFPO-C(=O)-NH-CH$_2$CH$_2$-O-C(=O)-CH$_2$CH$_2$-SH | 0.5 g in 50 g EtOH |
| 6 | HFPO-C(=O)-NH-CH$_2$CH$_2$-O-CH$_2$CH$_2$-O-C(=O)-CH$_2$CH$_2$-SH | 0.27 g in 27 g EtOH |
| C-3 | C$_4$F$_9$SO$_2$-N(CH$_3$)-CH$_2$CH$_2$-O-C(=O)-CH$_2$CH$_2$-SH | 0.5 g in 50 g EtOH |
| C-4 | H$_3$C-(CH$_2$)$_{17}$-NH-C(=O)-CH$_2$CH$_2$-SH | 10 mM in EtOH |
| C-5 | H$_3$C-(CH$_2$)$_{11}$-NH-C(=O)-CH$_2$CH$_2$-SH | 10 mM in EtOH |
| C-6 | H$_3$C-(CH$_2$)$_{7}$-NH-C(=O)-CH$_2$CH$_2$-SH | 10 mM in EtOH |
| C-7 | CF$_3$(CF$_2$)$_7$CH$_2$CH$_2$SH | 5 mM in EtOH |
| C-8 | CH$_3$(CH$_2$)$_{15}$SH | 5 mM in EtOH |

Preparation of Substrates Comprising Gold-Coated Polymer Films

Two types of polymer films were used to prepare gold-coated polymer films as substrates. One type of film was polyethylene naphthalate "PEN" film (Dupont™ Teijin® TEONEX® Q65FA, 100 micrometer thickness, E.I. Du Pont de Nemours and Company, Wilmington, Del.) in the form of approximately one-centimeter squares. A major surface of the PEN film was coated by sputtering with 70 nanometers of gold. The other type of film was polyethylene-terephthalate "PET" film (Dupont™ Teijin® TEONEX® ST504, 125 micrometer thickness, E. I. DuPont de Nemours and Company, Wilmington, Del.), also in the form of approximately one-centimeter squares. A major surface of the PET film was first coated by thermal evaporation (DV-502A thermal evaporator, Denton Vacuum, Moorestown, N.J.) with 20 angstroms of chromium and then coated with 70 nanometers of gold.

Procedure for Application of Patterning Compositions to Substrates

After metallization, the resulting gold-coated polymer films were immersed in each of the patterning compositions described in Table 1 above for varying time periods that are specified in the Examples below. The resulting immersion-treated metalized films were then rinsed with ethanol and dried with a nitrogen flow.

Etchants and Etching Procedure

After rinsing and drying, the immersion-treated metalized films (bearing a self-assembled monolayer (SAM) etch mask formed by immersion in the patterning composition) were immersed in various etchant solutions to challenge the SAM etch mask. Ferricyanide etchant, in-house-prepared KI/I$_2$ etchant, and commercial KI/I$_2$ etchant were used as the gold etchants.

The ferricyanide etchant solution was prepared by combining 0.042 grams of potassium ferrocyanide trihydrate (product no. 1-3114, J. T. Baker Chemical Company, Phillipsburg, N.J.), 0.329 grams of potassium ferricyanide (product no. 24,402-3, Aldrich Chemical Company, Milwaukee, Wis.), 1.90 grams of potassium thiosulfate (product number P24005, Pfaltz & Bauer, Inc., Waterbury, Conn.), 5.61 grams of potassium hydroxide ("Flake Caustic Potash," IMC Chemical Group, Inc., Niagara Falls, N.Y.), and 92.5 grams of deionized (DI) water. Each immersion-treated metalized film was immersed in this etchant solution for 45 minutes.

The in-house-prepared KI/I$_2$ etchant solution was prepared by combining 10 grams of potassium iodide (Aldrich Chemical Company, Milwaukee, Wis.), 5 grams of iodine (Aldrich Chemical Company, Milwaukee, Wis.), and 85 grams of DI water. Each immersion-treated metalized film was immersed in this etchant solution for 25 seconds.

The commercial $KI/I_2$ etchant was purchased from Transene Company (Silver Etchant TFS, Transene Company, Inc., Danvers, Mass.). Each immersion-treated metalized film was immersed in this etchant solution for 15 seconds.

Characterization of Etch Resistance

Visual observations were made to assess the etch resistance. Highly resistant SAMs allowed essentially only very limited or no etching of the gold coating underlying the SAM etch mask. Low-resistance SAMs allowed essentially unimpeded etching of the underlying gold coating. A 5-point scale was used for qualitatively rating etch resistance (5—highest resistance; 1—lowest resistance).

Examples 1-4 and Comparative Examples C-1 and C-2

A series of immersion-treated metalized PEN film squares (corresponding to the patterning compositions comprising Molecules 1-4, C-1, and C-2 in Table 1 above) was immersed in the ferricyanide etchant solution for 45 minutes and then water-rinsed. A second series of immersion-treated metalized PEN film squares (also corresponding to the patterning compositions comprising Molecules 1-4, C-1, and C-2 in Table 1 above) was immersed in the in-house-prepared $KI/I_2$ etchant solution for 25 seconds and then water-rinsed. All of the resulting samples were characterized according to the method described above, and the resulting etch resistance ratings are shown in Table 2 below.

Examples 5-6 and Comparative Examples C-3-C-6

A series of immersion-treated metalized PET film squares (corresponding to the patterning compositions comprising Molecules 5-6 and C-3-C-6 in Table 1 above) was immersed in the commercial $KI/I_2$ etchant solution for 15 seconds and then water-rinsed. All of the resulting samples were characterized according to the method described above, and the resulting etch resistance ratings are shown in Table 2 below.

Comparative Examples C-7 and C-8

A pair of immersion-treated metalized PEN film squares (corresponding to the patterning compositions comprising Molecules C-7, and C-8 in Table 1 above) was immersed in the ferricyanide etchant solution for 45 minutes and then water-rinsed. A second pair of immersion-treated metalized PEN film squares (also corresponding to the patterning compositions comprising Molecules C-7 and C-8 in Table 1 above) was immersed in the in-house-prepared $KI/I_2$ etchant solution for 25 seconds and then water-rinsed. All of the resulting samples were characterized according to the method described above, and the resulting etch resistance ratings are shown in Table 2 below.

Comparative Example C-9

A square of untreated metalized PEN film was immersed in the ferrocyanide etchant solution for 45 minutes and then water-rinsed. A second square of untreated metalized PEN film was immersed in the in-house-prepared $KI/I_2$ etchant for 25 seconds and then water-rinsed. Both of the resulting samples were characterized according to the method described above, and the resulting etch resistance ratings are shown in Table 2 below.

TABLE 2

| Example/Molecule No. | Molecule Structure | Etch Resistance (Ferricyanide) | Etch Resistance ($KI/I_2$) |
| --- | --- | --- | --- |
| 1 | HFPO-C(O)-NH-(CH2)3-N(CH3)-C(O)-(CH2)3-S-H | 5 | 3 |
| 2 | HFPO-C(O)-NH-(CH2)2-S-H | 2 | 1 |
| C-1 | $C_4F_9SO_2$-N(CH3)-(CH2)2-NH-C(O)-(CH2)3-S-H | 3 | 1 |
| 3 | [HFPO-C(O)-NH-(CH2)2-S-H]$_n$, n = 2 | 3 | 1 |
| C-2 | $C_4F_9SO_2$-N(CH3)-(CH2)2-SH | 4 | 1 |

TABLE 2-continued

| Example/ Molecule No. | Molecule Structure | Etch Resistance (Ferricyanide) | Etch Resistance (KI/$I_2$) |
|---|---|---|---|
| 4 | HFPO–[C(O)–NH–CH$_2$CH$_2$–N(H)–C(O)–CH$_2$CH$_2$–S–H]$_n$, n = 2 | 4 | 4 |
| 5 | HFPO–C(O)–N(H)–CH$_2$CH$_2$–O–C(O)–CH$_2$CH$_2$–S–H | N/A* | 5 |
| 6 | HFPO–C(O)–N(H)–CH$_2$CH$_2$–O–CH$_2$CH$_2$–O–C(O)–CH$_2$CH$_2$–S–H | N/A | 4 |
| C-3 | $C_4F_9SO_2$–N(CH$_3$)–CH$_2$CH$_2$–O–C(O)–CH$_2$CH$_2$–S–H | N/A | 2 |
| C-4 | H$_3$C–(CH$_2$)$_{15}$–N(H)–C(O)–CH$_2$CH$_2$–SH | N/A | 1 |
| C-5 | H$_3$C–(CH$_2$)$_{11}$–N(H)–C(O)–CH$_2$CH$_2$–SH | N/A | 1 |
| C-6 | H$_3$C–(CH$_2$)$_7$–N(H)–C(O)–CH$_2$CH$_2$–SH | N/A | 1 |
| C-7 | CF$_3$(CF$_2$)$_7$CH$_2$CH$_2$SH | 2 | 1 |
| C-8 | CH$_3$(CH$_2$)$_{15}$SH | 3 | 1 |
| C-9 | None | 1 | 1 |

*N/A = Not Applicable

Examples 7-11 and Comparative Examples C-10-C-15: Application by Microcontact Printing Stamp Fabrication A master tool for molding elastomeric stamps were generated by preparing patterns of photoresist (Shipley1818, Rohm and Haas Company, Philadelphia, Pa., a basic-soluble positive photoresist comprising propylene glycol monomethyl ether acetate, mixed cresol novolak resin, and a diazo photoactive compound) on 10-centimeter diameter silicon wafers. The design included a square array of square features (each square feature measuring about 95 micrometers by 95 micrometers; open area in masks and raised feature in the resulting stamps), with 5 micrometers space (recessed feature in the stamps) in between the square features. The photoresist was spin-cast onto the wafer to a thickness of approximately 1.8 micrometers. A separate binary chrome photomask with openings in the chrome that defined the square array of square features was used to expose the photoresist for patterning. After development of the photoresist, a master tool was provided that included a binary relief pattern comprising recessed features in the form of a square array of squares.

Two different stamp materials were used for molding elastomeric stamps. One stamp material was polydimethylsiloxane (PDMS, Sylgard™ 184, Dow Corning, Midland, Mich.). An elastomeric stamp was molded against the master tool by pouring uncured PDMS over the tool to a thickness of approximately 3.0 millimeters. The uncured PDMS in contact with the master tool was degassed by exposure to a vacuum and then cured for 2 hours at 70° C.

The other stamp material was an acrylate-terminated perfluoroalkylene oxide ("LTM diacrylate"), which had been synthesized by essentially the method described in U.S. Pat. No. 3,810,874 (Mitsch et al.). An elastomeric stamp was molded against the master tool by pouring uncured LTM diacrylate with a photoinitiator (Darocur™ 1173, 2-hydroxy-2-methyl-1-phenyl-propan-1-one, 0.5 weight percent, Ciba Specialty Chemicals Corp., Tarrytown, N.Y.) over the master tool to a thickness of approximately 3.0 millimeters. The uncured LTM diacrylate in contact with the master tool was cured under ultraviolet (UV) light (365 nm wavelength) from a mercury lamp (Blak-Ray™ XX-15BLB UV Bench Lamp, P/N 95-0042-06, UVP, LLC., Upland, Calif.) for 15 minutes.

After peeling from the master tool, each of the two stamps was provided with a relief pattern comprising raised square features approximately 1.8 micrometers in height, in the above-described square array pattern. Each of the two stamps was cut to a size of approximately 1.0-1.5 centimeters by 2 centimeters.

Inking

Each stamp was inked by immersion in a patterning composition for 30 minutes (inking time). After inking, the stamp was dried with a nitrogen flow for 1 minute.

Stamping

Gold-coated PET films (to serve as substrates) were prepared by the method described above (except that the films measured approximately 2 centimeters by 3 centimeters in area). After metallization, the films were stamped by using the above-described inked stamps.

The relief-patterned surface of the stamp was brought into contact with the gold-coated PET film for 30 seconds. During stamping, an additional mass was applied to the film-stamp assembly. The additional mass was a flat piece of glass weighing 120 grams. After stamping, the film was peeled from the stamp to provide a gold-coated PET film bearing a printed pattern.

Etching

After stamping, the gold-coated PET film with printed pattern was immersed in an etchant solution for selective etching and metal patterning. Both of the above-described in-house-prepared and commercial $KI/I_2$-based etchants were used. The printed metalized film was immersed in the etchant solution for 50 seconds (in-house-prepared etchant) or for 20 seconds (commercial etchant).

Characterization

After selective etching and metal patterning, the resulting metal patterns were characterized using an optical microscope (Model BH-2 equipped with a DP12 digital camera, Olympus America, Center Valley, Pa.) to judge the selectivity of the etching (the degree of protection and preservation of the gold in the printed regions of the substrate during the etching removal of gold from the unprinted regions). A selectivity quality factor of 1, 2, 3, 4, or 5 was assigned to describe the degree of selectivity that was exhibited (5 designated highest quality, with essentially no pinholes or erosion of the squares during etching; 1 designated lowest quality, with the array of squares being largely etched away).

The optical microscope was also used to assess the fidelity with which the intended metal pattern had been generated. The space between squares in the resulting metal pattern was measured and compared with the nominal space value of 5 micrometers. A dimension accuracy quality factor of 5, 4, 3, 2, or 1 was assigned, depending upon whether the measured space exceeded the nominal space by 0 micrometer, by more than 0 to less than or equal to 1.0 micrometer, by more than 1.0 to less than or equal to 3.0 micrometers, by more than 3.0 to less than or equal to 5.0 micrometers, or by more than 5.0 micrometers, respectively.

Examples 7-11 and Comparative Examples C-10-C-15

The patterning compositions described in Table 3 were printed on the above-described gold-coated PET film substrates and then etched by using the above-described procedures. In-house-prepared $KI/I_2$-based etchant was used for Example 7 and for Comparative Example C-14, and commercial $KI/I_2$ etchant was used for all other Examples and Comparative Examples. For Comparative Example C-15, blank (bearing no printed patterning composition) gold-coated PET film was immersed in the commercial $KI/I_2$-based etchant for 15 seconds.

Figure 4:
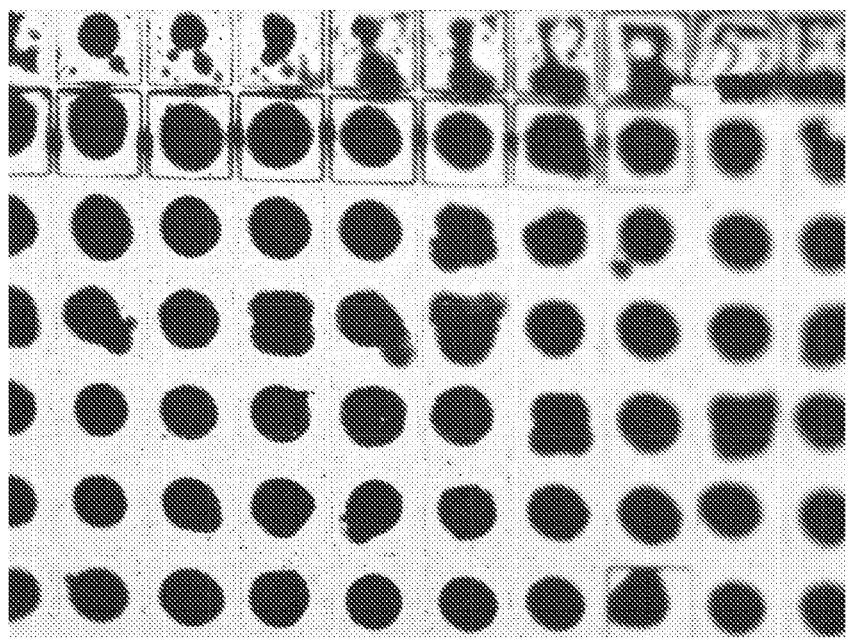
FIG. 4 is an optical photomicrograph (transmission mode) of the resulting gold-micropatterned substrate of Example 10 (dark region is gold).
Figure 5:
FIG. 5 is an optical photomicrograph (transmission mode) of the resulting gold-micropatterned substrate of Comparative Example C-10 (dark region is gold).
Figure 6:
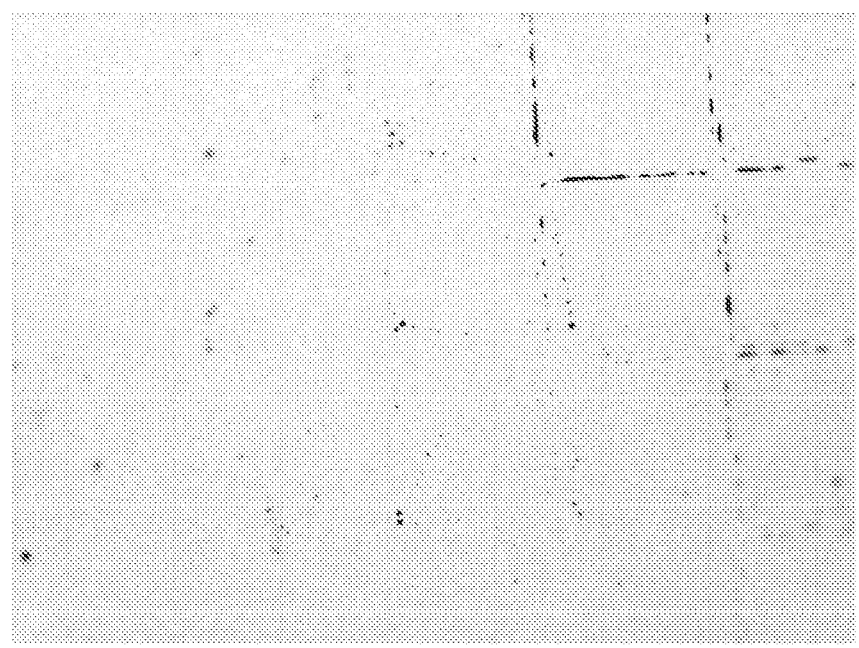
FIG. 6 is an optical photomicrograph (transmission mode) of the resulting etched substrate of Comparative Example C-14.
Figure 7:
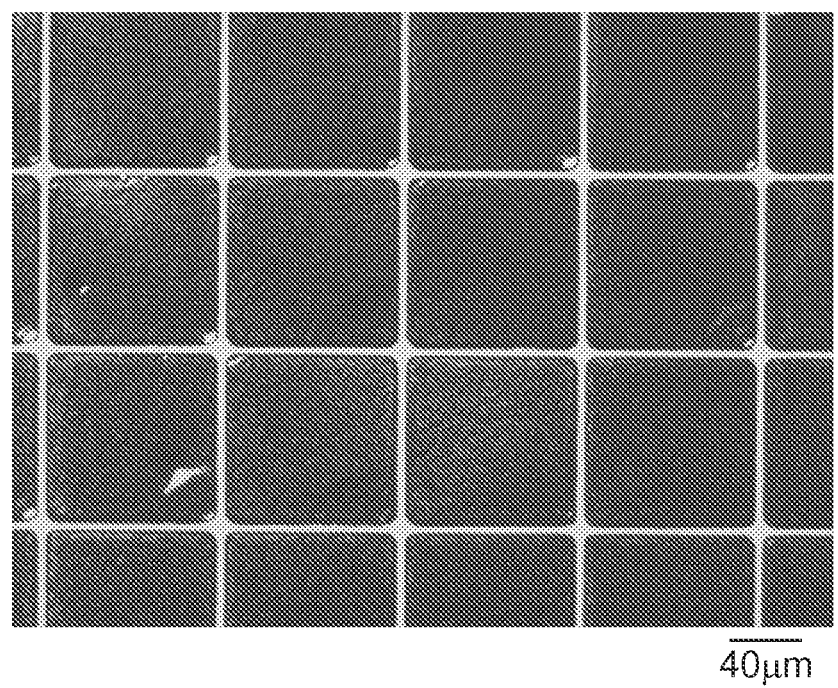
FIG. 7 is an optical photomicrograph (transmission mode) of the resulting gold-micropatterned substrate of Example 11 (dark region is gold).

The resulting etched substrates were characterized according to the above-described procedures, and the results are shown in Table 3 and in FIGS. 1-7. For Examples 7, 8, 9, 10, and 11, and Comparative Examples C-10 and C-14, the amount of gold removed from the functionalized region of the substrate per unit area after etching, expressed as a percentage of the amount of gold removed from the unfunctionalized region of the substrate per unit area, was estimated by using transmitted light attenuation in an optical microscope to be 8 percent (%), 5%, 10%, 10%, 14%, 67%, and 100%, respectively. For these estimates, in all cases a portion of the functionalized region was selected that was considered to be representative of the functionalized region. The portion of the functionalized region that was selected for analysis was smaller than the full contact region between the stamp and the substrate.

TABLE 3

| Example No. | Molecule No. in Tables 1 and 2 | Patterning Composition | Stamp Material | Selectivity Quality Factor | Dimension Accuracy Factor |
|---|---|---|---|---|---|
| 7 | 1 | 2.2 g in 180 g EtOH | PDMS | 4 | 2 |
| 8 | 4 | 4 g in 180 g EtOH | PDMS | 5 | 4 |
| 9 | 5 | 0.5 g in 50 g EtOH | PDMS | 5 | 1 |
| 10 | 6 | 0.27 g in 27 g EtOH | PDMS | 5 | 1 |
| C-10 | C-3 | 0.5 g in 50 g EtOH | PDMS | 2 | 3 |
| C-11 | C-4 | 10 mM in EtOH | PDMS | 1 | N/A* |
| C-12 | C-5 | 10 mM in EtOH | PDMS | 1 | N/A |
| C-13 | C-6 | 10 mM in EtOH | PDMS | 1 | N/A |
| C-14 | C-8 | 10 mM in EtOH | PDMS | 1 | N/A |
| C-15 | None | N/A | N/A | 1 | N/A |
| 11 | 5 | 0.5 g in 50 g EtOH | LTM Diacrylate | 4 | 5 |

*N/A = Not Applicable

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows.

We claim:

1. A process comprising (a) providing at least one substrate having at least one major surface comprising at least one elemental metal, at least one metal alloy, at least one metal-containing compound, or a combination thereof; (b) providing at least one patterning composition comprising at least one functionalizing molecule that is a perfluoropolyether organosulfur compound comprising at least one perfluoropolyether segment selected from F[CF(CF$_3$)CF$_2$O]$_a$CF(CF$_3$)—, wherein a has an average value of 4 to 20, and —CF(CF$_3$)(OCF$_2$CF(CF$_3$))$_b$OCF$_2$CF$_2$CF$_2$CF$_2$O(CF(CF$_3$)CF$_2$O)$_c$CF(CF$_3$)—, wherein b+c has an average value of 4 to 15; (c) applying said patterning composition to said major surface of said substrate in a manner so as to form at least one functionalized region and at least one unfunctionalized region of said major surface; and (d) etching at least a portion of said unfunctionalized region.

2. The process of claim 1, wherein said major surface comprises a metal selected from gold, silver, copper, platinum, palladium, nickel, and combinations thereof.

3. The process of claim 1, wherein said perfluoropolyether organosulfur compound is selected from perfluoropolyether thiol compounds, perfluoropolyether disulfide compounds, perfluoropolyether xanthate compounds, perfluoropolyether sulfide compounds, and combinations thereof comprising at least one said perfluoropolyether segment.

4. The process of claim 1, wherein said perfluoropolyether organosulfur compound is one of a class of perfluoropolyether thiol compounds that is represented by the following general formula (I):

R$_f$-[Q-(SH)$_x$]$_y$    (I)

wherein R$_f$ is a monovalent or divalent perfluoropolyether group selected from F[CF(CF$_3$)CF$_2$O]$_a$CF(CF$_3$)—, wherein a has an average value of 4 to 20, and —CF(CF$_3$)(OCF$_2$CF(CF$_3$))$_b$OCF$_2$CF$_2$CF$_2$CF$_2$O(CF(CF$_3$)CF$_2$O)$_c$CF(CF$_3$)—, wherein b+c has an average value of 4 to 15; Q is a divalent, trivalent, or tetravalent organic linking group; x is an integer of 1 to 3; and y is an integer of 1 or 2.

5. The process of claim 1, wherein said functionalizing molecule is an amide-linked perfluoropolyether organosulfur compound comprising at least one said perfluoropolyether segment.

6. The process of claim 5, wherein said functionalizing molecule is a said amide-linked perfluoropolyether organosulfur compound that comprises at least two carbonylimino moieties or that comprises at least one carbonylimino moiety and at least one carbonyloxy moiety.

7. The process of claim 5, wherein said amide-linked perfluoropolyether organosulfur compound is an amide-linked perfluoropolyether thiol compound that comprises a said perfluoropolyether segment, at least one mercapto group, and at least one intervening divalent carbonylimino moiety.

8. The process of claim 7, wherein said carbonylimino moiety is —C(=O)—NH—.

9. The process of claim 7, wherein said amide-linked perfluoropolyether thiol compound is one of a class that is represented by the following general formula (II):

R$_f$—[C(=O)—N(R)-Q-(SH)$_x$]$_y$    (II)

wherein R$_f$ is a monovalent or divalent perfluoropolyether group selected from F[CF(CF$_3$)CF$_2$O]$_a$CF(CF$_3$)—, wherein a has an average value of 4 to 20, and —CF(CF$_3$)(OCF$_2$CF(CF$_3$))$_b$OCF$_2$CF$_2$CF$_2$CF$_2$O(CF(CF$_3$)CF$_2$O)$_c$CF(CF$_3$)—, wherein b+c has an average value of 4 to 15; R is hydrogen or alkyl; Q is a divalent, trivalent, or tetravalent organic linking group; x is an integer of 1 to 3; and y is an integer of 1 or 2; or wherein said amide-linked perfluoropolyether thiol compound is one of a class that is represented by the following general formula (III):

R$_f$'—(O[CF(CF$_3$)CF$_2$O]$_a$CF(CF$_3$)—[C(=O)—N(R)-Q-(SH)$_x$])$_y$    (III)

wherein R$_f$' is a linear or branched perfluoroalkyl or perfluoroalkylene group; a has an average value of 4 to 20; R is hydrogen or alkyl; Q is a divalent, trivalent, or tetravalent organic linking group; x is an integer of 1 to 3; and y is an integer of 1 or 2.

10. The process of claim 1, wherein said patterning composition is applied by printing.

11. The process of claim 1, wherein said patterning composition is applied by microcontact printing.

12. The process of claim 1, wherein said functionalized region comprises a self-assembled monolayer (SAM) of said functionalizing molecule.

13. The process of claim 1, wherein said etching is chemical etching.

14. The process of claim 13, wherein said chemical etching is carried out by using a tri-iodide etchant system.

15. The process of claim 1, wherein said etching is carried out selectively.

16. A process comprising (a) providing at least one substrate having at least one major surface comprising gold; (b) providing at least one patterning composition comprising at least one functionalizing molecule that is an amide-linked perfluoropolyether organosulfur compound; (c) applying said patterning composition to said major surface of said substrate by microcontact printing so as to form at least one functionalized region and at least one unfunctionalized region of said major surface; and (d) selectively etching at least a portion of said unfunctionalized region by using a tri-iodide chemical etchant system.

17. The process of claim 14, wherein said tri-iodide etchant system is a potassium iodide/iodine-based etchant and said major surface comprises gold or silver.

18. A process comprising (a) providing at least one substrate having at least one major surface comprising at least one elemental metal, at least one metal alloy, at least one metal-containing compound, or a combination thereof; (b) providing at least one patterning composition comprising at least one functionalizing molecule that is an amide-linked perfluoropolyether organosulfur compound; (c) applying said patterning composition to said major surface of said substrate in a manner so as to form at least one functionalized region and at least one unfunctionalized region of said major surface; and (d) etching at least a portion of said unfunctionalized region.

* * * * *

UNITED STATES PATENT AND TRADEMARK OFFICE
CERTIFICATE OF CORRECTION

PATENT NO. : 8,858,813 B2
APPLICATION NO. : 13/130320
DATED : October 14, 2014
INVENTOR(S) : Lijun Zu et al.

It is certified that error appears in the above-identified patent and that said Letters Patent is hereby corrected as shown below:

In the Specification

Column 8
Line 19, delete "$(C_pF_{2p-1}O)$—" and insert -- $(C_pF_{2p+1}O)$— --, therefor.
Line 23, delete "$O)O_2F_4O)_qCF_2$" and insert -- $O)n(C_2F_4O)_qCF_2$— --, therefor.

Signed and Sealed this
Seventh Day of April, 2015

Michelle K. Lee
*Director of the United States Patent and Trademark Office*